(12) United States Patent
Ziegler et al.

(10) Patent No.: US 7,917,313 B2
(45) Date of Patent: Mar. 29, 2011

(54) METHOD FOR MONITORING A FLUID TRANSFER PROCESS

(75) Inventors: Guenter Ziegler, Polling (DE); Peter Wenzig, Munich (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 371 days.

(21) Appl. No.: 12/199,117

(22) Filed: Aug. 27, 2008

(65) Prior Publication Data

US 2009/0070049 A1    Mar. 12, 2009

(30) Foreign Application Priority Data

Aug. 27, 2007    (EP) .................................... 07016732

(51) Int. Cl.
 *G01F 23/00*    (2006.01)
(52) U.S. Cl. ............... 702/50; 702/12; 702/22; 702/23; 702/25; 702/30; 702/98; 702/100; 702/138; 702/140; 73/1.57; 73/37; 73/1.74; 73/863.01
(58) Field of Classification Search .................... 702/12, 702/22, 26, 30, 50, 98, 100, 138, 140, 23; 73/1.57, 1.74, 37, 863.01
See application file for complete search history.

(56) References Cited

U.S. PATENT DOCUMENTS

| | | | |
|---|---|---|---|
| 5,540,081 A | 7/1996 | Takeda et al. | |
| 6,281,517 B1 | 8/2001 | Burkhardt et al. | |
| 6,456,944 B1 | 9/2002 | Burkhardt et al. | |
| 6,938,504 B2 | 9/2005 | Camenisch | |
| 2004/0089051 A1 | 5/2004 | Camenisch | |
| 2007/0177986 A1* | 8/2007 | Leibfried ..................... | 417/44.2 |

FOREIGN PATENT DOCUMENTS

| | | |
|---|---|---|
| EP | 0499714 A1 | 8/1992 |
| EP | 0499714 B1 | 8/1992 |
| EP | 07016732.5 | 2/2008 |
| WO | 9208545 A1 | 5/1992 |
| WO | 9853325 A1 | 11/1998 |
| WO | 0188549 A1 | 11/2001 |
| WO | 02073215 A3 | 9/2002 |

* cited by examiner

*Primary Examiner* — Sujoy K Kundu
(74) *Attorney, Agent, or Firm* — Vivien Banholzer; M. Reza Savari

(57) ABSTRACT

The present invention relates to a method for monitoring a fluid transfer process, including the steps: providing an allowable pressure profile; detecting a pressure occurring in the course of the fluid transfer process; comparing detected pressure with the allowable pressure profile and signaling an error, if the detected pressure is not within the allowable pressure profile. The allowable pressure profile is defined by interpolation points, the interpolation points being based on a probability function representing a family of pressure courses of a plurality of fluid transfer processes. The allowable pressure profile can be divided into at least two distinct process sections, each section corresponding to a distinct process phase of the fluid transfer process. The probability function is calculated from a family of test pressure curves and reflects the statistical behavior of the pipette system. The present invention further relates to a computer readable medium for storing interpolation point information as well as to a kit-of-parts comprising a device implementing the inventive method, together with a computer readable medium for storing interpolation point information.

18 Claims, 9 Drawing Sheets

METHOD FOR MONITORING A FLUID TRANSFER PROCESS

CROSS-REFERENCES TO RELATED APPLICATIONS

The present application claims the benefit of EP Appl. No. 07016732.5 filed Aug. 27, 2007, the entire contents of which is hereby incorporated herein by reference in its entirety.

FIELD OF THE INVENTION

The present invention relates to a method for monitoring the transfer of fluid, in particular gas, by observing the pressure of the fluid. Further, the present invention relates to a method for monitoring the operation of the pipette.

BACKGROUND OF THE INVENTION

Volume transfer and flow velocity can be verified by monitoring the pressure in a device for transferring fluid. In the technical field of pipette systems it is known to monitor the pressure of a gas volume in the pipette filled with liquid, wherein the liquid seals the gas volume.

DESCRIPTION OF PRIOR ART

The application WO 02/073215 A2 discloses a method to evaluate a liquid dosing process in a container which is at least partially filled with gas. The temporal course of the pressure in the container is measured over the entire duration of the dosing process. The course of the pressure over time is compared to a pressure target value field, which is a function of time. Thus, upper and lower limiting curves define the target value field as a function of time. The target value field is defined by the average pressure course acquired in a number of runs and a predefined tolerance interval. Alternatively, the upper and the lower curve of the target value field is identical to an envelope of the pressure courses acquired in a number of runs and a predefined tolerance interval. While using the average does not distinguish between stable runs and runs with natural fluctuations, the envelope is defined by random characteristics due to random fluctuations, and, therefore, does not appropriately reflect the behavior of the system. Further, WO 02/073215 teaches to use equidistant sample values for defining a tolerance interval. Thus, WO 02/073215 teaches an equidistant sampling pattern with a high sampling frequency for sampling values defining limit curves. The sample values are provided in an equidistant pattern with a certain sample frequency. In other words, the sample values defining the tolerance interval are positioned in a periodical pattern.

The application WO 01/88549 A1 discloses a method to analyze a measured pressure profile by performing several tests. The tests include counting the number of crossings between the pressure curve and a limit, counting the number of inflection points of the pressure curve or counting the number of points on the pressure curve at which the slope is zero. In particular, upper and lower thresholds are discussed, which are defined by two predetermined values. The tests described in this document involve complex mathematical algorithms. For each test, an individual algorithm depending on the respective test is provided.

Application WO 98/53325 relates to methods for fluid handling comprising a continuous monitoring of the pressure. The pressure is integrated over time in order to determine the transferred volume. Further, predetermined pressure limits are provided which are defined by averaging the pressure over time and adding a predefined constant tolerance value.

An apparatus for monitoring pipetting operations is disclosed in EP 0 982 593 A1. In this application, the monitoring is based on optical measurements using a light beam. Threshold intensities are stored as reference values for verifying the pipetting operation.

Application EP 0 990 909 A1 discloses an analyzer for monitoring pipetting operations comprising the comparison of actual pressure sensor values to associated threshold values. If threshold values are exceeded, the ongoing process is repeated in order to correct the respective error.

WO 92/08545 describes a sample pipetting method in which an air pressure change is monitored for providing a surface level of aspirated fluid. The method further comprises observing pressure values falling outside predetermined values of a predetermined normal aspiration pressure interval. For each of the certain number of pressure measurements, a predefined interval is given.

All methods known in the prior art are based on threshold values or tolerance interval which are defined by constant parameters or are given as a continuous function of time. Thus, if the threshold values are given as a function of time, a large amount of information has to be processed in order to define the threshold values and to compare the threshold values with measured values. For preventing incorrect error detections, a high resolution and therefore a high number of data points defining the threshold must be stored, transferred to and processed by evaluation means. Reducing the resolution of the threshold over time in prior art systems necessarily leads to reduced precision in the evaluation process and a higher probability of false error detections. In the prior art, there is a direct dependency between reduced resolution of the threshold and a reduced reliability of error detection. Further, the prior art does not adequately reflect the behavior of the pipette system. Rather, methods according to the prior art lead to error tolerance areas which do not appropriately reflect the system behavior for a number of runs and are defined by random characteristics. None of the prior art systems involves monitoring by tolerance areas which truly reflect the system behavior and are based on detailed observations.

The present invention provides a method for monitoring a fluid transferred process.

SUMMARY OF THE INVENTION

The present invention relates to a method for monitoring a fluid transfer process, including the steps: providing an allowable pressure profile; detecting a pressure occurring in the course of the fluid transfer process; comparing detected pressure with the allowable pressure profile and signaling an error, if the detected pressure is not within the allowable pressure profile. The allowable pressure profile is defined by interpolation points, the interpolation points being based on a probability function representing a family of pressure courses of a plurality of fluid transfer processes. The allowable pressure profile can be divided into at least two distinct process sections, each section corresponding to a distinct process phase of the fluid transfer process. The probability function is calculated from a family of test pressure curves and reflects the statistical behavior of the pipette system. The present invention further relates to a computer readable medium for storing interpolation point information as well as to a kit-of-parts comprising a device implementing the inventive method, together with a computer readable medium for storing interpolation point information.

In a certain aspect, the invention relates to a method for monitoring a fluid transfer process, comprising: providing an allowable pressure profile, detecting a pressure occurring in the course of the fluid transfer process, comparing the detected pressure with the allowable pressure profile, signaling an error, if the detected pressure is not within the allowable pressure profile, wherein the allowable pressure profile is defined by interpolation points, the interpolation points being based on a probability function representing a family of pressure courses (710) of a plurality of fluid transfer processes.

In another aspect the invention relates to a computer readable medium for use in the method of the invention hereinabove, the computer readable medium storing interpolation points or information for directly or indirectly retrieving interpolation points from a data base or from a correspondence table, the interpolation points defining at least one of the sections of the allowable pressure profile.

In a further aspect, the invention relates to a kit-of-parts, comprising: at least one fluid transport device adapted for a fluid transfer process monitored by the method according to a method comprising: providing an allowable pressure profile, detecting a pressure occurring in the course of the fluid transfer process, comparing the detected pressure with the allowable pressure profile, signaling an error, if the detected pressure is not within the allowable pressure profile, wherein the allowable pressure profile is defined by interpolation points, the interpolation points being based on a probability function representing a family of pressure courses of a plurality of fluid transfer processes, terminating the fluid transfer process as well as suspending further fluid transfer processes, if the error signaled, and at least one computer readable medium storing interpolation points or information for directly or indirectly retrieving interpolation points from a data base or from a correspondence table, the interpolation points defining at least one of the sections of the allowable pressure profile, wherein the interpolation points stored on the computer readable medium correspond to the allowable pressure profile corresponding to the at least one fluid transport device.

DETAILED DESCRIPTION OF THE INVENTION

In one embodiment, the method uses interpolation points derived from a probability function, the probability function being provided by combining a plurality of test runs, i.e. by statistically combining a family of pressure curves of the same or of a similar fluid transfer process. The interpolation points are aligned with or are based on the probability function as a function of process time for a predefined, constant statistic parameter of the probability function, e.g. variance.

The present invention allows precise error detection in a fluid transfer process at a reduced storage and processing complexity by comparing the pressure with an allowable pressure profile defined by interpolation points specific to process phases of the fluid transfer process. In this way, the definition of the allowable pressure profile is adapted to the properties of the respective shape of the limit curve. In the same way, the interpolation points defining the allowable pressure profile are adapted to the properties of the fluid transfer process and its respective distinct phases. By dedicating the interpolation points to certain process phases, the resolution used for reproducing the allowable pressure profile can be significantly reduced without impairing the yielded precision of error detection. At the same time, the limit curves appropriately reflect the system behavior without any random influence of statistical irregularities. Additionally, no statistical information is lost by averaging the measured pressure curves. Rather, all fluctuations (which form the major part of the relevant system behavior) are appropriately reflected. Further, the occurrence of an error can be easily assigned to a process phase by referring to the interpolation points of the allowable pressure profile and the respective interval defined by the interpolation points. In an embodiment, if the measured pressure of the monitored pipette process is outside the allowable pressure profile, the respective probe related to the monitored process is flagged or otherwise invalidated. Additionally or alternatively, all recorded data related to the monitored process is communicated to an external error analyses tool as exported data, for example as an error message or in context of an error message. In this way, adequate responses on the occurrence of an error can be easily provided.

The concept underlying the invention is to define an allowable pressure profile as a function of time by significant interpolation points. In this way, interpolation data can be stored with an optimized entropy. Even if only a reduced number of interpolation points are used, all significant characteristics of the allowable pressure profile are reproduced since the definition or selection of the interpolation points addresses the inherent properties of the limit curve and the inherent properties and characteristics of the system. In this way, the error detection reflects all important properties of the monitored fluid transfer process. According to invention, the interpolation points are derived from the complete set of stochastic information of the measured test pressure curves without neglecting relevant system behavior, e.g. by averaging. Thus, the interpolation points and the allowable pressure profile is based on the complete information of empirical data. The concept underlying the invention further involves to monitor a number or family of test pressure curves and to extract the relevant characteristics by addressing all relevant statistical information. Therefore, all test pressure curves are adequately reflected by "summing" the test curve properties by calculating the variance as a function of time (together with the average as a function of time). According to the invention, the resulting statistical data of the test curves are mapped on a probability density function which is given as parameterized equation. The equation reflects the underlying system (for example by a Gaussian function, if the pressure fluctuations base on a high number of mutually independent processes), while the parameters of the equation (for a Gaussian probability function: variance $\sigma$ and average m) reflect the physical properties of the implemented pipette system. Since the stochastic data is appropriately reflected by mapping the measured data on a suitable probability function, the system behavior can be represented by few interpolation points without losing significant characteristics. In the embodiment based on a Gaussian function, both parameters can be easily derived from the data, i.e. by calculating the average as a function of time as well as the sum of squared distances between average and measured pressure as a function of time. Thus, the mapping can be implemented without high computational costs by performing these calculations.

Thus, the average as well as the variance are calculated and mapped onto a given probability function as a function of time as described above. The parameters of the probability function adequately reflect the real system, together with the probability function itself. In an embodiment, the parameterized probability function (e.g. Gaussian) is used to calculate maximum and minimum limit courses by calculating respective pressure min/max pairs (negative/positive deviation) corresponding to a given variance $\sigma$=const. In a certain embodiment, a plurality of pairs are calculated to adequately represent the probability function for a constant variance as a function of time. The pairs can be arranged periodically. The resolution/sample frequency of the min/max pairs can equal to the resolution/sample frequency of the measured pressure curves or can by less, e.g. only ½, ¼, ⅛... 1/256. In contrast to the prior art, in which envelopes (i.e. the maximum fluctuations) of a number of pressure curves, wherein the pressure curves having the highest error define the envelope, the minimum/maximum limit courses according to the invention reflect the overall behavior and do not immoderately emphasize single outliers.

At least one of the interpolation points defining the allowable pressure profile is derived from these maximum/minimum limit courses formed of the min/max pairs. In a certain embodiment, at least one interpolation is identical to an element of a min/max pair. Further, at least one interpolation point is equal to an element, i.e. a max or a min coordinate, of a min/max pair plus an additional safety margin, e.g. represented by an additional safety margin added to the corresponding pressure value, in order to reduce the probability of false error detections. The additional safety margin can be a constant, predefined value or can be an individual input of an user interface. According to a certain embodiment, the user interface is interactive and shows interpolation points (which can be connected to a line) as well as at least one of: test pressure curves, an error value representing to the difference between allowable pressure profile and the minimum/maximum limit courses, other allowable pressure profiles and a probability function as a function of time or for a certain point of time.

The interpolation points are designated to certain distinct process phases in order to distinguish between distinct physical processes occurring during the fluid transfer process. Thus, the interpolation points or each of the interpolation points comprises pressure value data as well as time value data both being specific to the shape of a standard pressure course and/or being specific to the respective process sections. Depending on the shape of a maximum and minimum limit course derived from of a family of measured pressure courses in a process phase, two or more data sets for two or more specific time points are sufficient to define the allowable pressure profile within this process phase.

According to the invention, maximum and minimum limit courses are approximated by the allowable pressure profile defined by the interpolation points. In a certain embodiment, the interpolation points defined the allowable pressure profile for at least a part of the process phase. Further, the maximum and minimum limit courses form the bases for the selection or setting of interpolation points representing the allowable pressure profile. Since the maximum and minimum limit courses as well as the measured pressure profiles for certain process phase are coherent and can be represented or approximated by simple geometrical forms, the reduction of interpolation points according to the invention does not significantly impair the reliability of the monitoring process. As a simple geometrical form, a straight line, two or more intersecting lines with different slopes or a negative exponential course approximated with a few lines or data points can be used. Since a pressure curve basically consists of process phases or sections thereof showing pressure courses of a simple geometry, the low resolution and coarse approximations of this pressure profile section only marginally reduce the precision of the monitoring method. Therefore, a sufficient approximation provided by a minimum of stored information can be accomplished by reproducing an allowable pressure profile section by section, whereby each section relates to a certain self-contained process phase. In an embodiment, only one physical process dominates the fluid transfer process during one process phase or process phase section. Further, process phases with distinct underlying physical processes but with similar or coherent pressure courses over time can be approximated by one common subset of interpolation points, in particular, if the pressure profile of one process section continues or repeats the pressure profile of a subsequent process section. The sections can further relate to basic curve shapes, regardless of physical processes, each section being related to one basic curve shape like a straight line, an angle or the like which can be reproduced by only a few interpolation points without substantial imprecision.

The present invention benefits from continuous, uniform sections of pressure profiles (e.g. during which only one physical process dominates the shape of the pressure profile) and eliminates interpolation points with less information and only negligible impact on the reproduced pressure profile. According to the invention, only interpolation points significant to a pressure profile are stored and processed wherein the significance of the interpolation point is derived from a change of the physical process dominating the fluid transfer and/or is derived from a fundamental change of the shape of the pressure profile. Distinct process phases can be defined by distinct underlying physical processes dominating the process phase. Additionally, distinct process phases can be defined by the shape of the pressure profile or by sections of the allowable pressure profile which have distinct geometrical properties, e.g. can be divided by an inflection point or by a discontinuity of the first derivation of a reference pressure profile (which is approximated by the allowable pressure profile). Further, waveforms e.g. the simple geometrical forms mentioned above can be correlated with the pressure courses or with the minimum/maximum limits to represent the curves or limits with standard forms. In an embodiment, the standard forms or waveforms are provided as pre-stored data. In contrast to the inflexible and rigid time pattern defining the allowable pressure profile, the invention uses interpolation points including variable time information for adapting the tolerance limits to the curve characteristics, i.e. shape, curvature and slope.

According to the invention, the approximation is based on interpolation points tailored to the reference pressure profile defined by test pressure curves and the properties of the shape of the reference pressure profile. As mentioned above, the interpolation points are derived from stochastic data assessment based on test pressure curves. Therefore, the interpolation points inherently reflect the stochastic behavior of the system and inherently reflect the basic characteristics of the reference pressure profile. Further, the approximated allowable pressure profile represents the reference pressure profile further reflecting tolerance values related to the respective process phase or to the fluid transfer process. The interpolation points can further be combined with reference information representing a certain basic shape or a certain geometrical form of a set of pre-stored basic shapes. Further, parameters can be added in order to further define the respective basic shape. In a certain embodiment, straight lines are used defined by two points lying on the straight line by two endpoints between which the line extends or by a coordinate pair combined with slope information. According to the invention, the term "interpolation point" can be any data which directly or indirectly defines the shape and position of a section of the allowable pressure profile, for example incorporating a time value related to a specific arbitrary position along the time axis (t-axis).

In a simple implementation, an interpolation point is a coordinate pair defined by the pressure value and the time value, the allowable pressure profile being defined by straight connection lines between the interpolation points. In this way, an upper as well as a lower limit of the allowable pressure profile can be defined. Further, if the interpolation points are pressure/time coordinate pairs, other interpolations can be carried out to provide the allowable pressure profile, for example polynomial interpolation or an appropriate series expansion. The interpolation points can be combined with parameters further defining the series expansion or the polynomial interpolation. In a yet further implementation, an interpolation point comprises information related to a location on the pressure-time diagram and refer to a certain curve shape or curve section of a predefined set of curves or curve shapes. Thus, the allowable pressure profile can be defined by retrieving a specific shape of a set of shapes, for example by using an index or a reference and by placing the curve sections to an appropriate location according to the coordinate given by the interpolation points. Additionally, the shape can be further defined by additional shape parameter information being part or being linked with a reference point or base point.

According to the invention, the allowable pressure profile represents a reference pressure profile in an interpolated way and is divided into at least two distinct process sections, each process section corresponding to a distinct process phase of the fluid transfer process. If the fluid transfer process is a step of pulling liquid into a chamber or in a pipette by applying vacuum, the process can be divided into the sections: establishing a vacuum pressure by increasing a volume, begin of liquid transfer of external liquid into the chamber or pipette, relaxation of the pressure difference by liquid transferred into the chamber, and approximating a stable condition or asymptote with reduced or negligible transfer of liquid. Further definitions of a process section can relate to piston movement phases, i.e. start or end of piston movement, acceleration or deceleration of the piston of a phase of piston movement with constant velocity.

Additionally, an initiation phase can precede the step of establishing a vacuum pressure (or the step of producing an overpressure), during which no pressure difference between a chamber or pipette and the examined environment is established and the means for providing the vacuum as well as the measurement devices are initiated. The initiation phase can further be defined by a predetermined time interval or delay. Further, the fluid transfer process can comprise the process sections: begin of the transfer of gas from the examined environment into a chamber or pipette due to exhausted liquid volume, transfer of gas into the liquid volume, relaxation of the pressure difference due to gas transfer into the pipette or chamber and approximation of a stable status with absent or negligible gas transfer, corresponding to a pressure difference of zero. Further process transfer sections can be the begin of liquid transfer due to break down of surface tension or capillary forces, a piston movement interval, during which a piston is moved in order to change a volume, passive liquid movement interval, during which the volume is constant and liquid is transferred due to pressure differences and aspiration or dispensation phases, during which a piston is moved in order to change a volume. Of course, instead of a piston, other means for pumping gas or liquid can be used and similar phases can be defined. The volume directly adjoining the piston can be filled with gas or liquid which is moved by the piston movement. This volume is directly or indirectly connected to the volume receiving or delivering the liquid which is to be transferred.

Of course, similar fluid transfer processes can be monitored, for example a dispensing process or sip- and spit-processes. In a certain embodiment, dispensing process comprises the process sections: changing volume in order to provide a pressure difference and transfer of fluid from a chamber or pipette to the outside. An aspirating process can comprise the same or complementary phases. In the same way, a dispensing process comprises similar or complementary process sections of a transfer process based on aspirating. Therefore, a dispensing process can comprise the process sections: establishing an overpressure in a chamber or in a pipette, begin of the liquid transfer from the pipette or chamber to external environment, relaxation of the pressure in the pipette or chamber and approximation of the pressure in the chamber or pipette to the external pressure, i.e. approximation to a pressure difference of zero. In general, the process phases can partly overlap such that one process section does not necessarily show a one-to-one correspondence to the physical process phases.

Rather, process phases can overlap such that the respective process section of the pressure profile is defined by the beginning of a first process and the end of a following physical process. In particular, process sections of process phases can be combined, if the respective pressure profile can be adequately interpolated with a corresponding subset of interpolation points. Further, two or more process phases can be merged together, if they belong to the same operation and/or if the allowable pressure profile can be represented by one common curve shape. For example, the beginning of a liquid transfer relaxation as well as the approximation to a stable value can be represented by one subset of interpolation points or by more than one subset of interpolation points. A process phase can correspond to a basic curve shape in a one-to-one correspondence. However, depending on the process phase, more than one basic shape might be necessary to represent the process phase, or one basic shape can be used to approximate more than one (consecutive) process phases.

As already described above, (physical) process phases correspond to specific forms in the pressure curve and vice versa. Thus, instead of focusing on the process phases when defining the process sections (and thus the respective interpolation points), begin and end of simple and elemental geometrical forms in the pressure curve can be used, regardless of the underlying process phase.

According to a certain embodiment of the invention the allowable pressure profile is derived from a number of runs of the same fluid transfer process during which the pressure has been measured. In this way, a family of pressure courses is acquired as a function of time wherein each of the individual courses relate to one run. A frequency distribution of the acquired family is provided by mapping all pressure courses in the same pressure-time diagram. In this diagram, the minimum pressure limits and the maximum pressure limits of all runs as well as an area or a line corresponding to an average can be detected. According a certain embodiment, for each or for a plurality of time points, the pressure values of the runs are mapped on a distribution function, for example the Gaussian distribution. Thus, the family of pressure courses can be empirically combined and represented by a Gaussian distribution having a deviation which is a function of time. In an embodiment according to the invention, at least one interpolation point is defined by the a certain probability value (or certain deviation) of the Gaussian probability distribution on which test or reference pressure curves have been mapped. The distribution stochastically reflects the characteristics of the pressure curves, and consequently of the real system. The certain value of the Gaussian probability distribution is a pressure value for a certain deviation, e.g. $N \cdot \sigma$, $N=3, 4, 5, 6, 7, 8, 9, 10, 11, 12$. Alternatively, the interpolation point can be given by the actual time value of the respective probability distribution and a probability value or probability density value. Thus, empirically derived Gaussian distribution for a certain point of time at a predefined deviation, for example $3\sigma$ or 6σ gives a min/max pair, the min/max pairs of all points of time defining the minimum/maximum course as a function of time. The time information of the interpolation point can correspond to the start, the end or to a point of time between the start and the end of a process section. Further, in an embodiment all or at least one of the interpolation points corresponds to a deviation of the empirically provided Gaussian distribution lower than their predefined variances, i.e. lower than 3σ or 6σ. In a certain embodiment, at least one interpolation point is located on a minimum or maximum course. In a certain embodiment, at least one interpolation point corresponds to a point or coordinate of the maximum or minimum course and an additional margin, which is added to the respective pressure value in order to broaden the allowable pressure profile for the respective section or point of time. In a certain embodiment, a minimum limit as well as a maximum limit is defined which corresponds to a predefined variance, deviation, standard deviation, probability pair (i.e. two probabilities with the same probability density) or probability density of the Gaussian distribution. These values can be predefined or can be input or provided otherwise and can directly used as interpolation point or can be used to indirectly provide at least interpolation point, wherein the respective coordinate on the maximum/minimum course are used as a basis. The lines defined by the predefined variances of the empirical Gaussian distribution can correspond to the boundaries or the minimum and maximum limit courses, respectively of the empirically provided Gaussian distribution with variances equal to the predefined variances. In particular, the reference pressure profile can be provided and stored as a deviation in the course of time and the mean pressure value as a function of time. Again, according to the invention, the minimum/maximum courses are based on probability distributions, on which a complete set of empirical data is mapped. In contrast thereto, the maximum/minimum limits in the prior art only reflect one pressure curve, i.e. the pressure curve (or section thereof) with the highest deviation from average.

The allowable pressure profile is defined by an upper and a lower curve which are the results of the interpolation of the interpolation points. In order to detect an error, a measured or detected pressure is compared with the upper and the lower curve in order to detect, whether the detected pressure lies in the allowable pressure profile. The upper curve and the lower curve can be individually defined by the interpolation points. Alternatively, the lower curve is defined by the interpolation points and the upper curve is derived from the lower curve by additional distance information defining the geometrical relation between the upper curve and the lower curve. In this way, the lower curve forms a base curve and a set of corresponding relative values is used to define the upper curve starting from the base curve. Of course, also the upper curve can be used as base curve and the lower curve can be derived from the upper curve using the relative values. The relative values correspond to a tolerance width which is equivalent to the distance between the upper and the lower curve and thus, defines the span of the pressure profile. Further, the interpolation point can be used as base point, together with slope information such that the base point and the slope value define the course of the pressure profile, for example a straight line. Thus, the pressure profile is formed of combination of interpolation points and a set of slopes, each slope corresponding to one interpolation point. Of course, the definition of the allowable pressure profile based on interpolation points (and further information) can be combined with the definitions of the allowable pressure profile, e.g. using predefined curve shapes or other geometrical forms defined by further parameters.

In general, the allowable pressure profile can be defined by: pressure-time coordinate pairs, predefined curve shapes, parameters further defining the curve shape, corresponding slopes or information concerning the rotation angle of the shapes as well as by references referring to pre-stored curve information and/or referring to data relating to other process phases, for example in the case of repetitions. Curve shapes can be given as an equation and parameters as well as by a list of pressure-time pairs, e.g. in a look up table or another buffer or storage device. Before comparing the detected pressure with the allowable pressure profile, intermediate curves or intermediate values can be calculated from the interpolation points. Alternatively, the detected pressure value can be compared with the allowable pressure profile by combination of extrapolating interpolation points and a comparison. The respective values can be stored as digitalized/quantisized time values and digitalized/quantisized pressure values with a given resolution. The term quantisized describes mapping of continuous values onto a number of discrete values. Quantisized values are the result of mapping continuous values onto a finite number of values, which is known from conversions of analogue signals onto discrete digital values. The mapping is inherently linked with errors called discretization errors resulting from the difference between a value of an analogue signal, which is continuous as regards the quantity, and the corresponding digital value, on which the value of the analogue signal is mapped. Further, the pressure profile can have a resolution over time, which is lower than the respective sample rate of the detected pressure. For example, a series of ten detected pressure points can be compared with one and the same value of the allowable pressure profile after a new value of the allowable pressure profile is provided. In other words, the allowable pressure profile can be provided in a plurality of steps, each step having a constant pressure course. The allowable pressure profile can be stored as look-up table. For example, only an actual and the following process section of the allowable pressure profile can be provided in the look-up table, the look-up table corresponding to a respective shifting window of the allowable pressure profile. If the upper and the lower curve are defined by straight lines, adders can be used to define the allowable pressure profile, the adders repeatedly adding the same number, whereby the number corresponds to the actual slope of the allowable pressure profile (i.e. of the upper or lower curve).

In a particular embodiment, only one interpolation point of the allowable pressure profile is given as a starting point, together with slope values, each slope value defining a slope in a respective process section. In this way, the upper and the lower curve can be defined by an initial interpolation point and by repeatedly adding the slope value (which can be positive or negative or zero). In this way, a subset of interpolation points of a process section is represented by an interpolation point and a set of slope values, together with information about the correspondence of the individual slope values and respective sections.

If the step of comparing the detected pressure with the allowable pressure profile (i.e. with the upper and the lower curve) leads to the result that the detected pressure is not within the allowable pressure profile, an error is signaled, for example by outputting an error signal to an output port. In a certain embodiment, the error signal does not only comprise the information that the detected pressure is not inside the allowable pressure profile, but gives additional information about the type of error by referring to the individual process section in which the error occurred. According to an embodiment, upon occurrence of an error, the pressure data of the actual run of the concerned pipette is transmitted to an data interface, e.g. together with error information. In particular, data of the pertinent process phase is transmitted. The transmitted data can cover the complete run or only the relevant process phase or phases, e.g. the phase during which the error occurred and/or at least one of the following phases. One run can relate to one pipette pr to a group or all pipette of a multi pipette system. In particular, the data of the pipette at which the error has been measured is transmitted. Advantageously, the data or error information comprises information identifying the pipette the error or measurement is related to. This applies in particular for pipette systems with more than one pipette. Further, pressure data of precedent pipette processes can by transmitted, alone or in combination with the data related to the actual run. In particular, the data of at least one precedent process (same sample and/or distinct sample) is transmitted, which has been carried out by the pipette related to the actual error. Further, the pressure data of other pipettes belonging to the same group or system can be transmitted. In a certain embodiment, the pressure data of all pipettes is transmitted, which have been used to process the same sample. Since the error can be caused by abnormal characteristics of a probe, related errors (concerning the same sample) which have not been detected yet can be identified. In a certain embodiment, raw pressure data is transmitted upon occurrence of an error. In a simplified embodiment, the sample related to the pipette process during which the error occurred is flagged as erroneous.

Each pressure section can be related to at least one process phase providing further information related to the occurred error. In one implementation of the invention, the error signal comprises an index or a reference, which defines the process section. In a certain embodiment, the error signal comprises information about the probe which has been processed during the occurrence of the pipette error. This reference can be identical to the reference denoting the process section. Further, the error information can comprise a reference referring to the respective process phase, for example the same reference which is used to denote (or refer to) the individual process phase.

The monitored fluid transfer process is for example a pull-in/push-out process in which volume changes lead to a transfer of fluid, for example liquid into the chamber or from the chamber to the environment. The transfer of liquid through an opening of the chamber is dependent on properties of the opening, for example length, diameter, dimensions of spacers located at the tip, angle between pipette and liquid surface, or other parameters. If pipettes are used, the pipette tips form the opening of the chamber, which is at least partly provided by the pipette. In an embodiment, exchangeable pipettes or pipette tips are used together with a common pipette basis. Since the pressure curve depends on spacers located at the opening of the pipette tip, the distance between pipette tip and probe chamber wall, the immersion angle etc., in an embodiment the same pipette tip is used for at least a group of or all pipette processes carried with a certain probe. In this way, errors or erroneous monitoring resulting from slight differences between two pipette tips, both used for the same sample, can be prevented. Of course, using only one pipette tip per probe or group of process chambers related to one probe prevents cross contaminations.

In a plurality of pipettes, the properties of the respective tips or openings can vary. Therefore, if one or more pipettes are dedicated to one or more fluid transfer process (es), the pipettes can be measured in a preceding test transfer process leading to a curve or a family of curves which are used as reference. In this way, the behavior and all characteristics of pipettes and the respective system can be reflected in the allowable reference profile as a result of a overall assessment of statistical behavior. According to an aspect of the invention, the reference curve provided by the test process or test processes is used as a basis for the allowable pressure profile such that variations due to manufacturing can be compensated. Further, a group of pipettes can be measured and the resulting reference curve can be used as a basis for another group of pipettes provided that both groups have been produced by the same or identical manufacturing process.

In an embodiment, a batch of pipettes (e.g. replaceable pipettes) is used to perform test transfer processes on all, some, or at least one of the pipettes of the batch, the respective pressure course or courses are acquired and an allowable pressure profile related to this batch is generated based on a measured course or courses. The allowable pressure profile related to this batch can be referred to when carrying out the method for monitoring the fluid transfer process, provided, that one of the pipettes of the tested batch is used. The allowable pressure profile of the batch is for example stored in a retrievable manner, for example in an accessible data base (for example stored in and accessible through the internet) stored on a computer readable medium separated from the batch or on a computer readable medium combined with the batch forming a kit, for example a barcode storing the allowable pressure profile attached or printed on a package carrying the batch of pipette tips. Alternatively, RFIDs can be used, which store the allowable pressure profile. The data representing the allowable pressure profile can be stored directly with the batch or can be stored externally, the batch being related to a reference which can be used to retrieve, establish or provide the allowable pressure profile. For example, a serial number is stored with the batch and the serial number is used to retrieve interpolation point from a data base provided in the monitored system or in an external data base. In an embodiment, interpolation points or other data providing the allowable pressure profile is stored as described above. The batch is a group of pipettes referring to the same charge or lot, which has been manufactured under the same circumstances and therefore provides similar properties. In this way, variations of the properties of the pipettes due to varying manufacturing processes or manufacturing parameters can be compensated and can be addressed during monitoring. In another embodiment, a batch is tested and the pressure courses are classified. In this embodiment, the batch is delivered with a classification code, the classification code referring to a pre-stored pressure profile. For example, three classes can be provided (narrow, standard and wide referring to the opening of the pipettes and/or referring to the equivalent flow resistance at the opening, which can depend from ridges, spacers and/surface constitution at the opening). Thus, the allowable pressure profile can be selected according to the classification. Alternatively, a given allowable pressure profile can be modified according to this classification. As an example, the classification "narrow" relates to a pressure profile with a slower increase or decrease of pressure and a longer duration of a time interval between establishing a pressure difference and approximating a pressure difference of zero.

In addition to the interpolation points defining the allowable pressure profile, further properties of the fluid transfer process can be used to adapt the allowable pressure profile to the circumstances, in which the respective pipette is used. Thus, fluid properties as well as properties of the fluid connection can be taken into account when defining the allowable pressure profile or when providing a correction of the interpolation points. In particular, the allowable pressure profile can be adapted on the status of the pipette or the pipette tip, i.e. can have a different shape or bias, if the tip has already been used, i.e. the tip is wet, or if the tip is used for the first time and/or is not covered with liquid. If no related information is given and it is not known, if the tip is used the first time or is wet (as a result of a preceding pipette step), the allowable pressure profile can be broadened, e.g. by adding a respective margin to the upper/lower curve or to the interpolation points.

In order to precisely monitor the fluid transfer process, the pressure measurement device and/or the device providing the vacuum or overpressure is initialized before the fluid transfer process is carried out. During the initiation, the pressure sensor can be reset to zero. In this phase, the upper and lower curve of the allowable pressure profile is located at an adequate distance, for example a constant distance to both sides of the line corresponding to a pressure of zero. In order to calibrate the pressure sensor, the signal of the pressure sensor is set to zero by calibration means or by interpreting the signal of the pressure sensor at an applied pressure of p=0 Pa as a signal corresponding to p=0. The interpolation can be interpreted as an alignment of the scale to the measured pressure value. Further, the offset can be identified and subtracted from measure values. Further, in particular aspiration, an applied pressure different from p=0 Pa can be included into the interpretation of the pressure sensor signal. The pressure sensor can be calibrated before each run of the respective pipette system and/or can be calibrated after a pipette tip is connected to the system. In one embodiment, the system is calibrated before delivery. In an embodiment, a standard pressure is held for at least 50 sec-2 min before setting/calibration or is monitored for at least 50 sec-2 min and any variances in the course of time exceeding a threshold cause a calibration error and/or a repetition of calibration process. In one embodiment, a predefined amount of liquid is aspirated into the pipette causing a predefined vacuum pressure, e.g. 80 mbar. Then, the pressure sensor and the connected measurement system is set to this predefined vacuum pressure. Due to noise, sample errors and discretization errors, the pressure value can be different from zero even if the pressure is equal to zero. The term "discretization errors" describing the difference between analogue signals with continuous values and the mapping result, i.e. a number with finite resolution. In this application, "discrete" is according to the definition of standard ISO 2382-1, section: "discrete: Pertaining to data that consist of distinct elements, such as characters, or to physical quantities having a finite number of distinctly recognizable values, as well as to processes and functional units that use those data.". In particular, analog/digital converters are used to convert the analogue pressure sensor signal into a pressure value. Thus, during the initial phase, i.e. during a first process section at the start of the fluid transfer process, the width of the allowable pressure profile is selected to accommodate fluctuations resulting from amplification, A/D-conversion, noise or further error or noise sources. Therefore, at the initiation phase or at the first process section, the allowable pressure profile forms a corridor around a pressure of zero, for example with a constant width. The measurement system, including the pressure sensor, can have an overall tolerance of ±3%, ±2% or ±1% at maximum.

In an embodiment, the method for monitoring a fluid transfer process as described above is used for controlling the fluid transfer process, wherein, upon occurrence of an error, the fluid transfer process is suspended, for example immediately after detection of an error. Further, other process steps, e.g. incubation, mixing and/or other pipette processes can be suspended for the sample, which has been processed during occurrence of the error. In one embodiment, the pipette process, during which the error occurs is not suspended, but all pipette and/or other processes related to the same sample (i.e. the sample which has been processed during occurrence of the error). In another embodiment, no pipette processes are suspended. However, in this case, the concerned sample and/or the pipette tip is flagged and/or related error information is provided to a data interface. In another embodiment, all pipette processes with pipettes actually carrying liquid are not suspended but carried out until the liquid in the pipette is dispensed. In particular, the pressure difference is actively reduced or any further pressure generation is suspended, if an error occurs. In one embodiment, the pressure generating device, for example a pump and/or a piston is stopped. If other fluid transfer processes are carried out simultaneously in the same system, or if further fluid transfer processes are based on a fluid transfer process in which an error occurred, these further or simultaneous transfer processes are not carried out and respective probes are flagged or marked. In one embodiment, a sequence of interrelated fluid transfer processes is carried out completely, if an error occurs in a different fluid transfer process, however, no new sequence of transfer processes is started.

The method described above can be carried out by software, by hardware or by a combination thereof. In order to implement some or all features of the above described methods, the software is processed by a processing unit or by a controller, the method features, being defined by executable code and/or instructions. The code and/or the instructions can be stored on any readable device, for example any computer readable device which provides software and/or instructions to a processing unit adapted to perform one of the methods described above. The instructions can be stored together with information related to the definition of the allowable pressure profile on the same storage device.

The fluid transfer process is for example carried out by a pump connected to a pipette when the pump is adapted for pumping air or another gas, and the pipette is connected to the pump so as to transfer the pressure and volume differences generated by the pump to the pipette. In this way, liquid can be sucked into the pipette and can be forced out of the pipette. In an embodiment, the pipette comprises two parts, a reusable part like a pipette basis, to which a discardable part is connected, e.g. a pipette tip receiving, holding and/or supplying probe fluid. The pipette can comprise a filter segment, for example located between both parts or at a segment of the discardable part close to the reusable part or at a segment of the reusable part close to the discardable part. In an, embodiment, the filter has a pore size between 15 and 90 µm or less than 1000 µm, 500 µm, 200 µm or 100 µm. The discardable part is adapted for contacting probes, and isolates the liquid probes from the reusable part. In this way, the reusable part is not contaminated with the liquid. In an embodiment the pipette is filled with liquid provided by a preparation chamber, the preparation chamber being filled with at least 800 µl, for example at least 850 µl, 1 ml, 2 ml or 3 ml of probe liquid. In particular, the preparation chamber can be filled with approx. 850 µl, at least 850 µl or at least approx. 850 µl and at the most approx. 2.5 ml-3 ml. In another process type, the preparation chamber contains at least approx. 60 µl and at most 80 µl. Thus, the preparation chamber can contain a liquid volume of 50-3000 µl which is at least partly or completely processed (i.e. aspirated/dispended by the pipette. In a particular embodiment, the preparation chamber contains a liquid volume of 5-50 µl, 10-30 µl or ≦approx. 15 µl. Further, the volume of the preparation chamber can be between 500 µl and 20 ml, or between 850 µl and 3 ml. In a certain embodiment, the tip of the discardable part of the pipette has an inner diameter of 0.8 mm or between 0.2 and 3 mm, between 0.5 and 1.5 mm, or between 0.7 and 0.9 mm or approx. 1.2 mm.

The pipette tips can be provided in a batch of a plurality of discardable pipette parts having a maximum deviation of 15 or 10% related to the inner diameter of the tip. Further, the tips can comprise three or four equidistant spacers located on the plane comprising the opening. Additional deviations can occur by varying dimensions of the spacers or by contaminations of the spacers. In an embodiment, these deviations are addressed when defining the allowable pressure profile. According to one embodiment, the discardable tip encloses a volume of 2.5 ml, in particular between 0.5 and 20 ml, between 2 and 10 ml and between 2 and 3 ml. In another embodiment, the tip provides an inner volume of 100-500 µl, 200-400 µl or of 250-350 µl. If pipettes with a small inner volume are used, variations can be high, such that the allowable pressure profile is defined with high tolerances, i.e. with high distances between the upper and the lower curve defining the allowable pressure profile. High variations can further result from a small distance between pipette opening and wall, particles in the liquid, e.g. magnetic beads or slurry. In an embodiment, tolerance of the tip diameter is approx. 5% or less. Further, pipette tips with small volumes are related to a monitoring method with a reduced set of errors and a reduced set of distinct process sections. Small volumes can be defined by a volume less than 500 µl or less than 800 µl.

In an embodiment, the pressure sensor providing the pressure occurring in the course of the fluid transfer is in fluidic communication with the fluidic connection between a pump and a pipette. In a certain embodiment, the pressure sensor is located at a tap near the pump. The pressure sensor is for example adapted to sense pressures between ±20000 Pa, ±15000 Pa, ±10000 Pa, or ±8000 Pa. In particular, a pressure sensor with a usable pressure interval of approx. ±10000 Pa, 15000 Pa, 18000 Pa or 20000 Pa is used. Further, in particular for small volumes (e.g. smaller than 500 µl, 200 µl, 100 µl or 80 µl sample volume or pipette tip volume) pressure sensors with a usable pressure interval of approx. ±5000 Pa or ±3000 Pa are used. Further, the pressure sensor is adapted to follow a slope rate of at least 500 Pa/msec, 2000 Pa/msec, or at least 5000 Pa/msec with an error of less than 20%, 10%, 5%, 2%, 1% or 0.1%.

In an embodiment, the step of comparing is carried out with analog signals, i.e. with an analog pressure signal and at least one analog limit signal. In a certain embodiment, the comparison is carried out digitally and an analog/digital-converter is provided for converting analog pressure signals into digital pressure values with a resolution of at least 8 bit, 12 bit or 16 bit and a sample rate of at least 10 Hz, at least 50 Hz, 80 at least Hz, at least 100 Hz, at least 200 Hz, at least 1000 Hz, at least 10000 Hz, or at least 100 kHz.

The step of comparing the detected pressure with the allowable pressure profile can be carried out directly after detection of the pressure or after the detected pressure has been translated into a sequence of buffered pressure values. The comparison can be carried out for each detected pressure value, for a set of detected pressure values or for a plurality of pressure values related to a certain process section, time interval or similar.

If more than one pressure is to be compared with the allowable pressure profile, a sequence of buffered detected pressure values has to be compared with the respective section of the allowable pressure profile. In a further embodiment of the invention, a first derivative of the detected pressure course is compared with a respective allowable pressure profile. Further, other derivatives can be compared with reference profiles as defined above with regard to the allowable pressure profile. Further, the detected pressure as a function of time can be monitored in combination with its derivatives. For example, in addition to the monitoring process concerning the detected pressure curve, the slope of the detected pressure curve can be monitored in order to detect slopes lying above a certain threshold. Of course, the threshold can be defined in the same way as the allowable pressure profile is defined, such that the threshold is time-variant, defined by a subset of interpolation points depending on the individual process phases as described above with regard to a pressure curve.

BRIEF DESCRIPTION OF THE FIGURES

FIG. 1 shows a set or family of typical pressure courses 10 as measured by a pressure sensor in the course of a dispensing process. The dispensing process is performed by a piston moving an air volume. The air volume exerts a pressure on probe liquid located in the pipette. Further, the pressure can be produced in a buffer volume more or less continuously and a controllable valve selectively connects the buffer volume with a pipette. FIG. 1 further shows a minimum limit 20b and a maximum limit 20a extracted from the family of typical pressure courses 10, c.f. FIG. 8, (which have been measured beforehand with the same pipette or with similar pipettes) as well as a lower curve 30a and an upper curve 30b defining the allowable pressure profile 30 a, b. The allowable pressure profile approximates the minimum and the maximum limit 20a, b using interpolation points (depicted as squares), which are sequentially connected by respective straight lines. The interpolation points are grouped in an upper group forming the upper curve 30a, and a lower group forming the lower curve 30b. In FIG. 1, each interpolation point is defined by a coordinate pair, i.e. a pair comprising a pressure value and a corresponding time value. Further, an interpolation point of the lower curve can be associated to an interpolation point of the upper curve, both having the same time value. In FIG. 1, such a pair of interpolation points is depicted with t=40 ms. Further pairs with same time values can be found at the start and at the end of the upper und the lower curve, respectively. The interpolation points do not necessarily depict the start and the end of a process section but are positioned for a proper approximation and a reduced interpolation error as is explained more in detail below.

According to the invention, the upper as well as the lower curve (together forming the allowable pressure profile) can be divided into distinct process sections, each defined by a respective interpolation point or by respective interpolation points. According to the invention, the interpolation points are derived from minimum/maximum courses, the courses corresponding to a defined variance of a probability function, onto which empirical data of a number of test runs has been mapped. Thus, the distinction among process phases additionally helps derive the interpolation points from the minimum/maximum courses derived from the empirical data. In particular, a high additional margin can be added to the minimum/maximum courses in sections with high tolerances (e.g. tolerable gas bubbles in non-critical process phases). In the same way, only few additional margin could be added to minimum/maximum courses in sections with low tolerances, i.e. critical sections, in which a (substantial, non-tolerable) fluctuation indicates a substantial error. In FIG. 1, not all interpolation points are located at junction of a first process section and a second process section following or preceding the first process section. Rather, the interpolation points are located at positions relevant to the shape of the allowable pressure profile for representing or approximating the main characteristics of the shape of the maximum and minimum limit 20 *a, b*.

In FIG. 1, the x-axis shows time t in 10 ms, i.e. the numbers shown at the x-axis have to be multiplied by 10 in order to obtain the time in ms. In FIG. 1, a first process section is between t=0 and t=100 ms, a second process section is between t=100 ms and t=400 ms, a third process section is between t=400 ms and t=800 ms, a fourth process section is between t=800 ms and t=1300 ms, a fifth process section is between t=1300 ms and t=1600 ms and a sixth process section is between t=1600 ms and the end of the diagram at t=1700 ms. As already mentioned above, according to a certain embodiment of the invention, the pressure curve is subdivided into process sections. However, the invention can also been carried out without such a subdivision. According to the invention, the interpolation points are based on the upper and lower curve which in turn correspond to a probability function at a predefined variance. The (parameterized) probability function is a result of a set of test pressure curves, which are mapped onto a given probability function by adjusting or calculating the parameters of the probability function such that the probability function represents the test pressure curves with a given exactness. However, it is advantageous to locate or align the interpolation points with the process sections, e.g. with the respective start/end of the process section.

Figure 1:
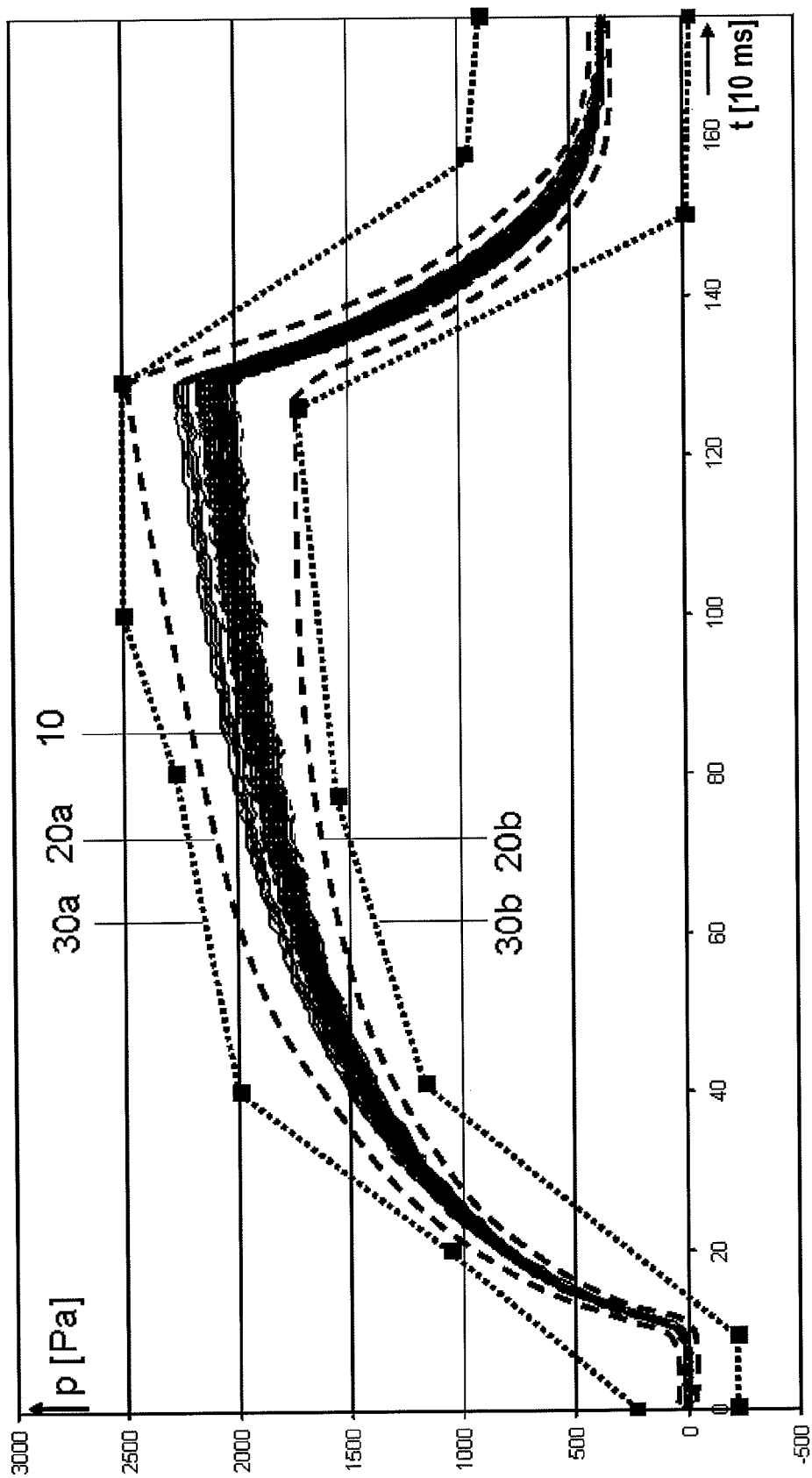
FIGS. 1-7 and 9 show typical pressure courses, together with an allowable pressure profile as defined in the method according to the invention.

As can be seen from in FIG. 1, the process sections do not correspond to the line sections defined by adjacent interpolation points in a one-to-one correspondence. Further, the physical processes occurring during the pipette process, i.e. initialization (p=0), piston displacement (corresponding to a rising pressure) and pressure balancing (corresponding to a falling pressure) are not represented by the process sections in a one-to-one correspondence. Rather, the division into process sections mainly addresses the relevant characteristics of the shape of the measured pressure courses 10 and the shape of the minimum and maximum limit 20 *a, b*. However, since physical processes are inherently reflected by the shape of pressure courses, some process sections can correlate with the respective physical processes. The position of the interpolation points can also correlate with the underlying physical process. However, the position of the interpolation points can be selected in order to minimize the approximation error resulting from the interpolation or to reflect a higher precision for certain sections than others. In particular, the time value of the interpolation point coordinate can be displaced from the start or the end of the respective process section to minimize the error due to interpolation, i.e. the error due to the approximation of the upper and the lower curve 30 *a, b* of the allowable pressure profile to the shape of the pressure courses and to the minimum and maximum limit 20 *a, b*. One and the same interpolation point can be the common interpolation point for two or more adjacent sections.

In one embodiment, the interpolation points are set according to a standard curve. In an embodiment, the standard curve corresponds to the minimum or maximum limit derived from a family of test curves via mapping onto a probability function. In a certain embodiment, at least one interpolation point is set or displaced according to an user input. For setting the position of the interpolation points, an error function is for example calculated according to an area or an area section between the minimum limit 20*b* and the lower curve 30*b* and between the maximum limit 20*a* and the upper curve 30*a*, respectively. Alternatively, the error function can also be based on the sum or integral of distances between the minimum limit 20*b* and the lower curve 30*b* and between the maximum limit 20*a* and the upper curve 30*a*. In an embodiment, the distances are the distances along a direction parallel to the p-axis and correspond to pressure values. Instead of distances and areas or area sections, the square or square root of the respective distance or area values can be used to form a basis for the error function. Additionally, the distances or areas can be weighted to reflect more or less sensitive areas having distinct precision requirements. For example, the weight is selected according to a predetermined weight function or depends on the slope, such that sections with high slopes have a higher weight than sections with low slopes. In this regard, e.g. the section in FIG. 1 between t=100 ms and t=300 ms could have a higher weight such that an error between interpolation by curves 30*a, b* and the maximum/minimum limit 20 *a, b* has a higher impact on the error function than other sections. For example between 400 ms and 1200 ms, the standards regarding the exactness of the pressure curve are higher leading to a higher weight of an error or to a lower distance between upper/lower curve and maximum/minimum limit, respectively than in other sections.

The error function can be displayed, together with a graph as depicted in FIG. 1, and a user interface can be given for interactively displaying and displacing interpolation points, together with a repeatedly updated error function value or error. Further, a positioning process for approximating curves 30 *a, b* to the maximum/minimum limit 20 *a, b* can be applied in order to provide or optimize the positions of the interpolation points forming curves 30 *a, b*. Such a positioning process can be carried out by a least mean square algorithm or by an iterative optimization process. Such an iterative process for example comprises the steps: providing an initialization position for at least two points, for example based on the maximum/minimum limit course, i.e. based on a predefined probability function prob=f(t)@ variance=const, e.g. 6σ, the parameter(s) of the probability function resulting from a family of test pressure curves (i.e. a number of runs with similar conditions), calculating an error function value, e.g. by using an error function as described above, displacing at least one of the interpolation points and repeating the steps of calculating and displacing. In one embodiment, the iterative process comprises: providing a number of interpolation points based on the maximum/minimum limit course, carrying out another number of runs and identifying the detected correct and/or false errors and/or the undetected errors based on the set interpolation points; and readjusting the interpolation points based on the number of correct/false errors and/or undetected errors. This embodiment can further comprise: selectively provoking an error during the another number of runs by changing conditions, for example by setting conditions onto a tolerable or intolerable operating condition. Such operating conditions can be: temperature, viscosity, flow resistance, presence of a certain number and size of particles or other operating conditions relevant to the performance of the pipette system.

In a certain embodiment, such a process further comprises one of the following steps: verifying, whether a point of one of the curves 30 *a, b* lies between the maximum/minimum limit 20 *a, b*; repositioning or displacing at least one interpolation point, if a point of one of the curves lies between the maximum/minimum limit, moving at least one of the curves farther away from the pressure courses 10; adding an interpolation point, if a point of one of the curves lies between the maximum/minimum limit; verifying the influence of a test interpolation point by calculating an error function between an upper or lower curve including the test interpolation point and the respective curve without the test interpolation point, the error function (e.g. one of the error functions described above) providing an influence value; deleting a test interpolation point, if the respective influence value is lower than a threshold; calculating the reduction of error for N consecutive iteration steps, and, if the reduction of error is higher than a threshold and the error value of one of the N iteration steps is higher than another threshold, adding an interpolation point. In an embodiment, an added interpolation point is added at a position near to an interpolation point positioned at a high distance to the respective maximum/minimum limit 20 a, b. Further an interpolation point can be added between two interpolation points positioned at the highest distance to the respective maximum/minimum limit 20 a, b. Still further, an interpolation point can be added at a position with a high or the highest slope of the maximum/minimum limit 20 a, b or of the pressure courses 10. In an embodiment, the iterative process described above is terminated after a predefined number of steps and/or if an error values is lower than a predetermined threshold.

If carried out with the graph as depicted in FIG. 1, the step of verifying the influence of interpolation point t=200 ms would result in a very low influence value since this point as well as both points adjacent to that point approximately form a straight line such that the shape of curve 30 a would not be changed significantly, if point t=200 ms would be omitted. Similarly, an error value calculated for points t=100 ms/p=−200 Pa and t=400 ms/p=1200 Pa is high (measured as area between the respective straight line and minimum limit 20b). The error is higher than a respective threshold and an additional interpolation point could be added, for example in the middle between both points. Thus, the added point could be optimised to better reflect the shape of the minimum limit 20b by displacing the added point towards the minimum limit 20 b. In certain process phases, a high tolerance can be provided intentionally by deleting inner interpolation points and/or by adding an additional distance to the interpolation points. This can be used to reflect variances in certain process phases which are higher than the variances in distinct process phases. Further, only some of the sections of the allowably pressure profile can be based on the statistically derived maximum/minimum limit course. In particular sections with high variances can be defined by interpolation points which do not base on test runs. In this way, the present invention allows particular adjustments and flexibility for certain sections. The interpolation points in theses sections can be input via an user interface.

In one embodiment, the displacement is carried out by repeatedly increasing the p-value of the added point by a step. The step size of the step can be constant or can be decreasing with the number of repetitions or iterations. In another embodiment, also the t-value of the added interpolation point is varied by another step size. Both step sizes or only one thereof can be selected according to a respective error value such that high step sizes are used, if the error value is high, and low step sizes are used, if the error value is low. The t-value and the p-value can be changed in an interleaved or alternating pattern or can be changed in two consecutive processes. In general, the processes described above are particularly adapted for the method of monitoring a fluid transfer process according to the invention and are not limited on dispersing processes as described in FIG. 1. Rather, the methods described above can be similarly used for an aspiration process having negative pressure values. Further, the described methods can be used in a periodically repeated sip-and-spit process. As described above, the method according to the invention can be used for monitoring a pipette process.

Figure 2:
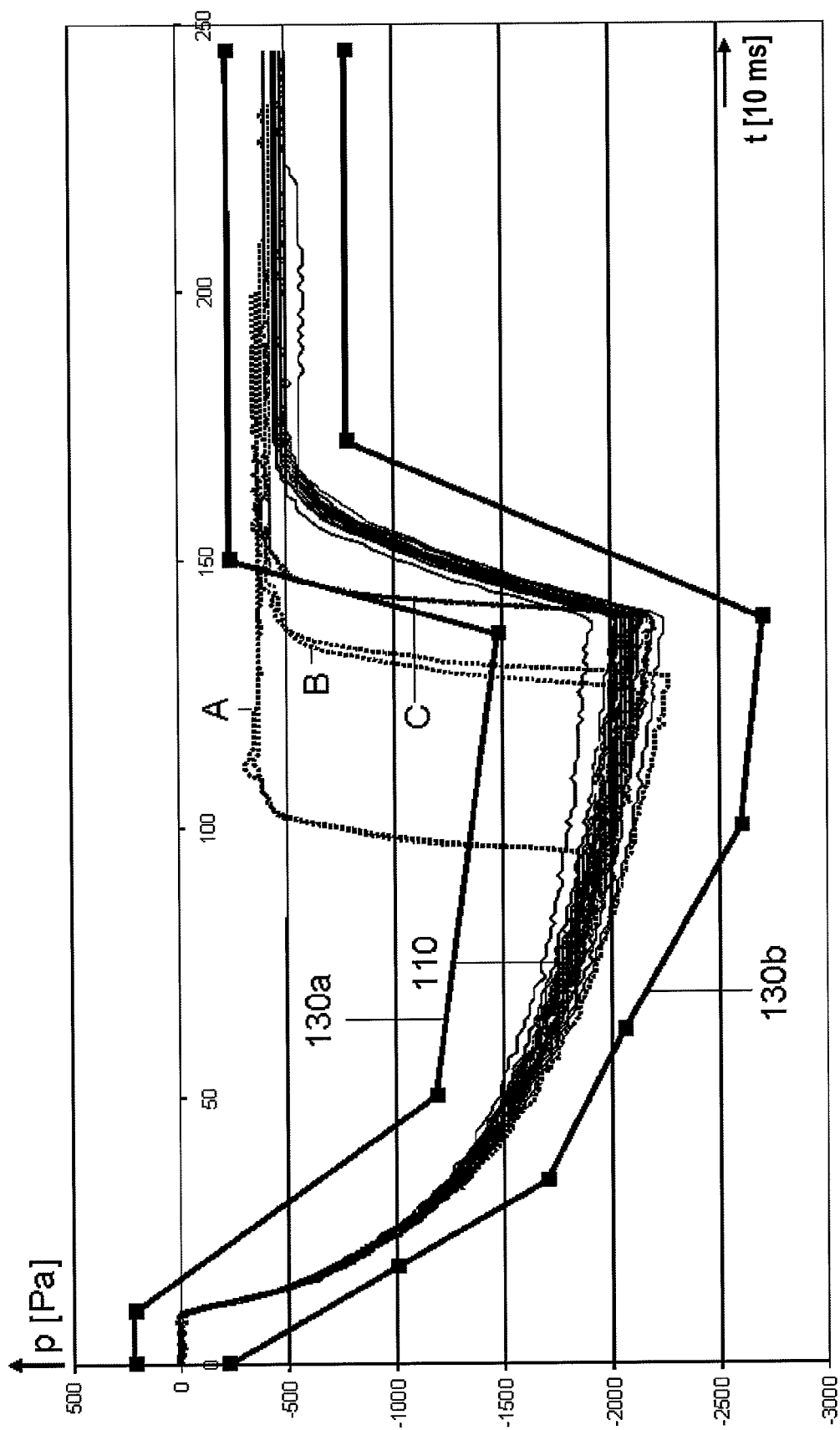

In FIG. 2, another typical pressure course as well as a lower and an upper curve 130a, b defined by interpolation points defined according to the invention are depicted. FIG. 2 relates to an aspiration process showing pressure course features, which are complementary and/or symmetrical to the features of the courses of FIG. 1. A family of pressure courses 110 has been provided by preceding test aspiration processes. Like in FIG. 1, interpolation points defining the upper and lower curves 130a, b of the allowable pressure profile are depicted as squares. Interpolation is performed by connecting interpolation points of the upper curve 130a as well as of the lower curve 130b with straight lines.

In FIG. 2, monitored pressure courses relating to a standard aspiration process, i.e. a process without errors, are located on the family of curves 110. The pressure courses of a standard aspiration process relate to the aspiration of a volume of 850 µl liquid. Further, in this standard aspiration process, the volume reduction caused by a pump as well as the inner form and the inner volume of the pipette itself is adapted for an aspiration process of 850 µl. The liquid volume can be contained in a receptacle with an inner volume of >850 µl, e.g. 1 ml, 2 ml or 3 ml. In other words, the process depicted in FIG. 2 is adapted to an aspiration of 850 µl; any external liquid exceeding this volume does not enter the pipette since the volume reduction of the aspiration process is automatically terminated at a volume difference ΔV=850 µl. Thus, liquid volumes of >850 µl located in the receptacle, e.g. 1000 ml, lead to similar pressure curves.

However, if the external liquid volume supplied to the pipette, i.e. to the tip of the pipette, is less than the standard volume of 850 µl, an aspiration error occurs. This aspiration error is caused by gas (e.g. air) entering the pipette after all external liquid has been pulled into the pipette. The gas is pulled into the pipette by the pressure difference caused by the volume difference between volume reduction of 850 µl provided by the pump and the insufficient external liquid volume supplied to the pipette. In other words, the gas is erroneously pulled into the pipette by the continuation of the aspiration process after the external liquid has been completely aspirated into pipette. Without monitoring the pressure, more gas is pulled into the pipette until the pumping process is terminated at 850 µl. However, the erroneous transfer of gas into the pipette is inherently connected with a fast and early reduction of the pressure difference. The aspiration of gas at the end of an pipette process can further be detected or verified by typical curve forms occurring at the following dispensing step, e.g. short peaks and/or a discontinuous $1^{st}$ derivation of the pressure curve, in particular at the beginning. As mentioned above, the movement of the pump can be stopped upon detection of an error. Alternatively or in combination therewith, an error can lead to a flag, an error signal, a termination of following process steps or similar events.

Curve A of FIG. 2 shows the pressure course for a an external liquid volume of 500 µl at a volume difference of 850 µl caused by the pump. Thus, the relaxation of the pressure course does not end at approx. t=1500 ms but earlier at approx. t=950 ms. As can be seen from FIG. 2, pressure course A rapidly leaves the allowable pressure profile defined by upper curve 130a and lower curve 130b. Thus, the method according to the invention allows to detect this error, to signal an error corresponding to the respective process section (e.g. last half of the liquid aspiration) and to relate the error to additional error information (e.g. upper curve 130a is crossed indicates that air enters the pipette). Curve B is related to an insufficient external liquid volume of 700 µl. Consequently, Curve B crosses the upper curve 130a at approx t=1300 ms, i.e. the point of time at which the external fluid is used up and external gas begins to enter the pipette. The method according to the invention allows perform respective reactions as already described with regard to curve A. Similarly, curve C shows a typical pressure course for an external volume of 800 µl and a volume difference of 850 µl caused by the pump. Thus, C does not show the relaxation as provided between approx. t=1400 ms and approx. t=1700 ms like the pressure courses of 110. Rather, curve C shows an abrupt reduction at approx. t=1400 ms to an asymptote level of p=−450 Pa. During this abrupt reduction, curve C crosses the upper curve 130a at approx. t=1450 ms.

For a person skilled in the art, FIG. 2 discloses the resulting modifications comprised by the invention, i.e. to move point t=1500 ms/p=−200 Pa more to the left, if an external volume of 800 µl shall be acceptable or to add an additional interpolation point e.g. at t=1400 ms/p=−300 Pa to upper curve 130a. Similarly, it is disclosed from FIG. 2 for a person skilled in the art to move point t=1500 ms/p=−200 Pa more to the right, if an external volume of 800 µl or even 820 µl shall be not be acceptable or to add an additional interpolation point e.g. at t=1450 ms/p=−800 Pa to upper curve 130a. In general, by adding or moving an interpolation point, the restrictions represented by the respective upper or lower curve can be modified to higher or lower standards or precision.

Further, a direct relationship between the slope occurring during relaxation and the kind of medium entering the pipette can be seen from FIG. 2. In FIG. 2, the movement of the pump is stopped immediately upon detection of an error (=pressure is outside the allowable pressure profile). For this reason as well as for the reduced viscosity, if gas is aspirated, the slope (as well as the maximum slope) occurring at the relaxation between t=1400 ms and t=1700 ms for an empty liquid reservoir (i.e. external liquid) is higher than for a non-erroneous process, during which liquid is continuously supplied to the pipette tip. Thus, the slope of the pressure course can be monitored, together with or as an alternative to the pressure course itself. Further, a section of a straight line arranged in a defined angle reflects the main features of a process section or process related to the start or to a first section of a relaxation process. With regard to FIG. 2, the pressure course between t=1400 ms and t=1600 ms can be well monitored by an upper curve section as defined by the connection between the interpolation points t=135 ms/p=−1500 Pa and t=150 ms/p=−200 Pa.

This upper curve section is used to monitor the start of the relaxation (end of volume or pressure variations by the pump) as well as the proper course of the relaxation, i.e. the kind of medium entering the pipette. The start is monitored by the proper position of the upper curve section whereas the kind of medium is monitored by the slope of the upper curve section. In general, these features can also be used to monitor the pipette process section in FIG. 1 at t>100 ms and at t>1200 ms as well as in FIG. 2 at t>100 ms.

Figure 3:
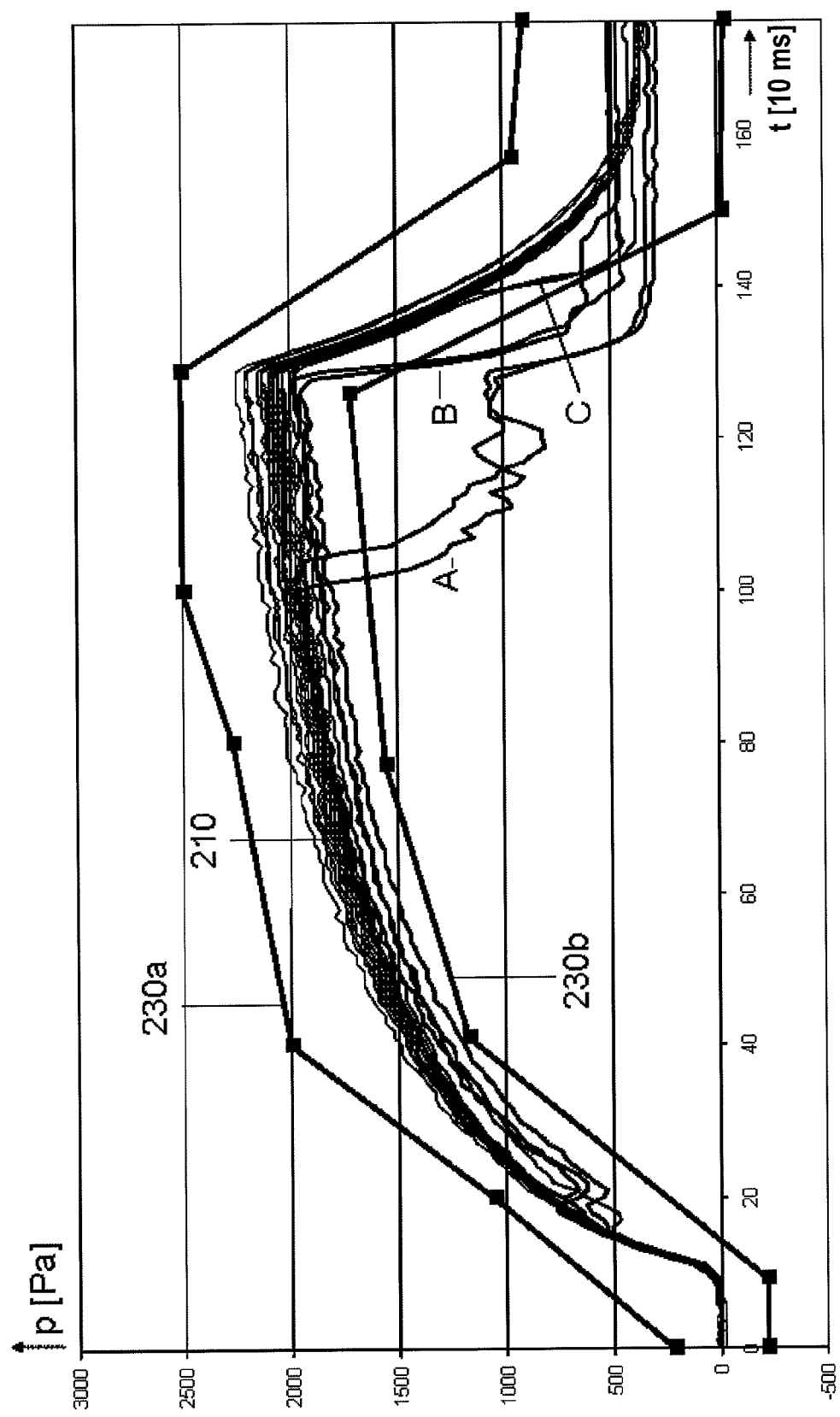

FIG. 3 shows the dispensing processes after the respective aspiration processes depicted in FIG. 2 with standard volume (850 µl, reference signs 110 and 210) and with reduced volume (A: 500 µl; B: 700; C: 800 µl). In FIGS. 2 and 3, identical or corresponding reference signs refer to the identical, corresponding or complementary features.

FIG. 3 shows a set or family of typical pressure courses 210 as measured by a pressure sensor in the course of a dispensing process. Similar to FIG. 2, this dispensing process is adapted for a liquid volume of 850 µl. Thus, the pump causes a total volume difference of 850 µl. The family of pressure courses 210 show standard processes. From this family 210, an upper curve 230a and a lower curve 230b are derived as described above and as further described in detail with regard to FIG. 8.

Upper curve 230a and lower curve 230b together define the allowable pressure profile. Similar to FIG. 2, Curve A of FIG. 3 shows the pressure course for an external liquid volume of 500 µl at a volume difference of 850 µl caused by the pump. Curve B is related to an insufficient internal liquid volume (i.e. the volume of liquid enclosed by the pipette) of 700 µl. Curve C shows a pressure course for an internal volume of 800 µl and a volume difference of 850 µl caused by the pump. Like in FIG. 2, the relaxation after termination of pump movement (or pressure/volume variation by the pump) at approx. t=1300 ms starts earlier for reduced volumes. Curve A (liquid volume of 500 µl instead of 850 µl) shows a start of relaxation at t=1000 ms (or t=1100 ms). Thus, curve A crosses the lower curve 230b at t=1000 ms/1100 ms. Curve A shows two measurements for the same conditions.

The relaxation after termination of pump movement for curves B and C starts synchronously to the relaxation of the standard processes. However, the relaxation of curves B and C is faster since gas instead of probe liquid is dispensed. Curve B shows this effect for t>1300 ms and curve C for t>1400 ms. In comparison to curves A, B and C in FIG. 2, the respective curves in FIG. 3 are less continuous and have a higher variance among processes with the same liquid volume. Thus, each of curves A, B and C in FIG. 3 has been measured and depicted twice.

Further, at the start of the first of relaxation process (i.e. the begin of the piston movement) Curves A, B and C show pressure fluctuations caused by small amounts of gas transferred through the pipette tip at this moment as well as caused by the compression of additional gas, which has entered the pipette due to lack of liquid volume during the preceding aspiration process. These fluctuations can be detected by monitoring the slope of the pressure course, i.e. the first derivation of the pressure vs. time. In one example, the detection is performed using a constant limit of 0 Pa/s for the pressure slope in the interval 100 ms<t<1200 ms. This limit can be reproduced by two interpolation points which are related to the pressure slope. In FIG. 2, this pressure slope limit would cause the detection of two errors for curve A: at t=180 ms and at t=1000 ms. In addition or as an alternative, the second derivation of the pressure course could be monitored using a tolerance interval defined by two pairs of interpolation points, both concerning the second deviation of the pressure course. In order to monitor the first derivation, maximum and minimum slopes could be obtained by a number of runs and a corresponding allowable pressure slope profile could be derived from the resulting statistics, similar to the maximum and minimum limit courses and the respective allowable pressure profile as defined above. Of course, other ways of defining a tolerance area (equivalent to the allowable pressure profile) for the slopes could by used.

Figure 4:
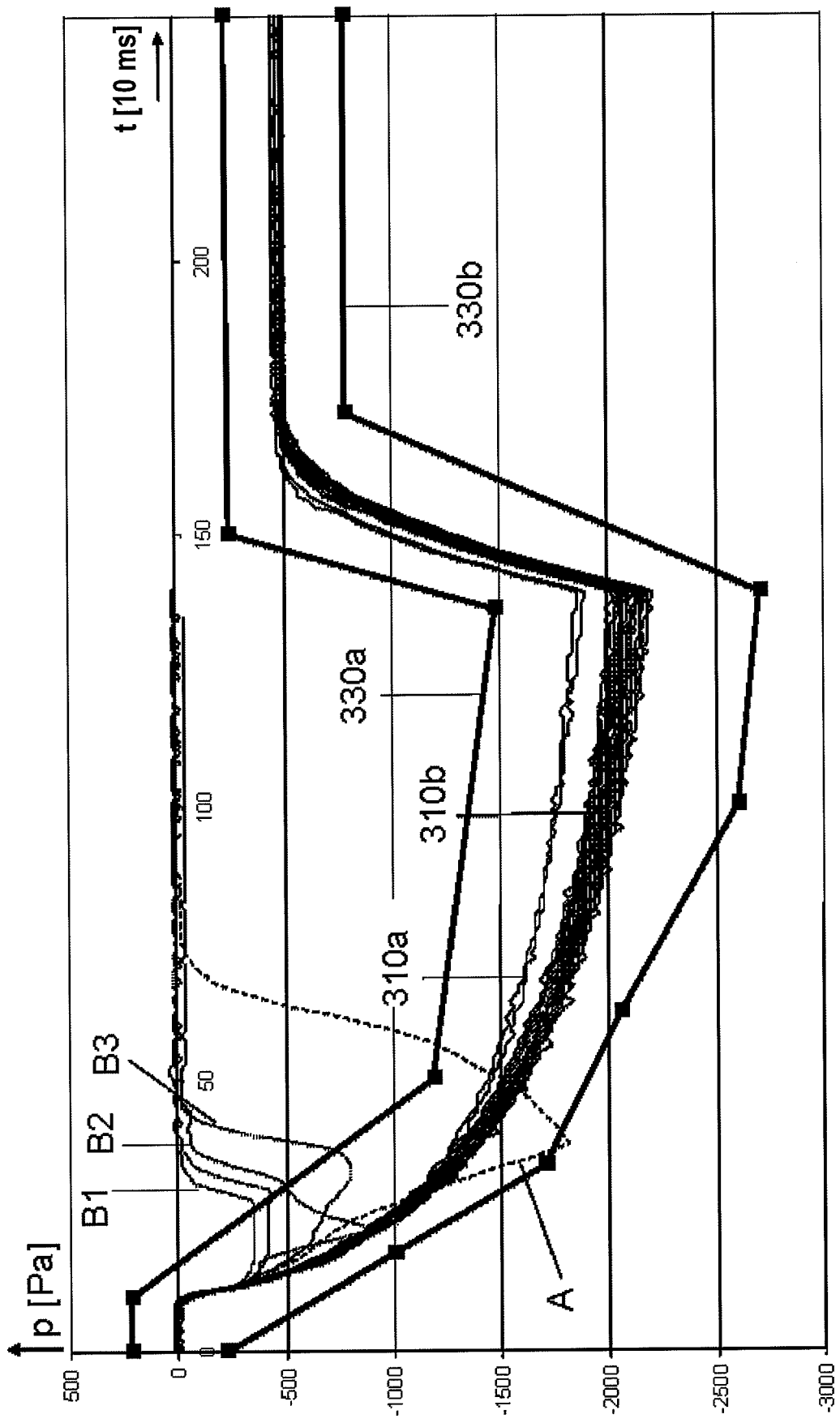

FIG. 4 shows a first family of pressure courses 310a and a second family of pressure courses 310b for an aspiration process. The first family 310a has been measured using a first receptacle in which the tip is immersed and the family 310a has been measured using a second receptacle in which the tip is immersed. The inner walls and the shape of the first and the second receptacle differ leading to differences regarding the flow and the flow resistance. The differences lead to different statistical behaviour as can be seen from FIG. 4. However, similar results can be obtained for different temperatures or if the first family 310a has been measured with a first batch or lot of pipette tips and the family 310b has been measured with a second batch or lot of pipette tips. The first batch and the second batch differ in the manufacturing process or manufacturer. The differences between the families reflect diameter and/or shape differences caused by tolerances in the manufacturing process. The pipette tips can be formed by extrusion of polymers like PP, PE or PU. In particular, if the pipette has small dimensions, these dimensions can vary according temperature, pressure, material mixture, extruder or other manufacturing parameters which influence the flow properties of the pipette. However, even if similar families are used, a variation as shown between family 310a and family 310b occurs for reused tips with particles positioned in the pipette or pipette tip. Further, the variations between family 310a and family 310b can be caused by different fluidic properties of the probe liquid, e.g. due to temperature, surface tension or other parameters influencing the viscosity of the probe liquid. In order to eliminate other influences, the tips can have the same status (wet/dry/unused) if the same process is tested. For aspiration test runs, the tip can be dry for all runs. In the same way, the tip is can be wet for all dispense steps.

In FIG. 4, curves B1-B3 relate to lack of external liquid such that an amount of zero or only a negligible amount of external liquid is aspirated into the pipette. Curves B1-B3 relate to aspiration processes during which only air or small droplets are aspirated into the pipette. The small droplets may be residuals of preceding processes performed in the reservoir supplying liquid to the pipette. Further, the aspiration of gas may be the result of solid or gel clusters partly obstructing the direct fluid connection between liquid and pipette tip such that ambient air is aspired by the pipette. Thus, in FIG. 4, the area between the t-axis and the curves B1-B3 reflects only a small amount of aspirated liquid. B1-B3 reach an upper curve 330a (relating to an allowable pressure profile) and no further pressure is produced since the pumping process is terminated. Thus, B1-B3 rapidly fall back on a pressure of p=0 Pa.

Curve A of FIG. 4 shows an aspiration process with a clotted sample. In this case, particles of clotted blood or other protein form obstacles for the liquid flow. Thus, the decrease in pressure is higher than the decrease for standard aspiration processes, e.g. 310b, and a lower curve 330b (relating to the allowable pressure profile) is crossed. Upon crossing, pressure generation is terminated and the pressure falls back to p=0 Pa. Additionally or alternatively, the slope of the pressure course could by used for detecting clothing, e.g. by providing a limit for the slope using one or two interpolation points relating to the slope of the pressure course. In FIG. 4, curve A is shown as dashed line.

Figure 5:
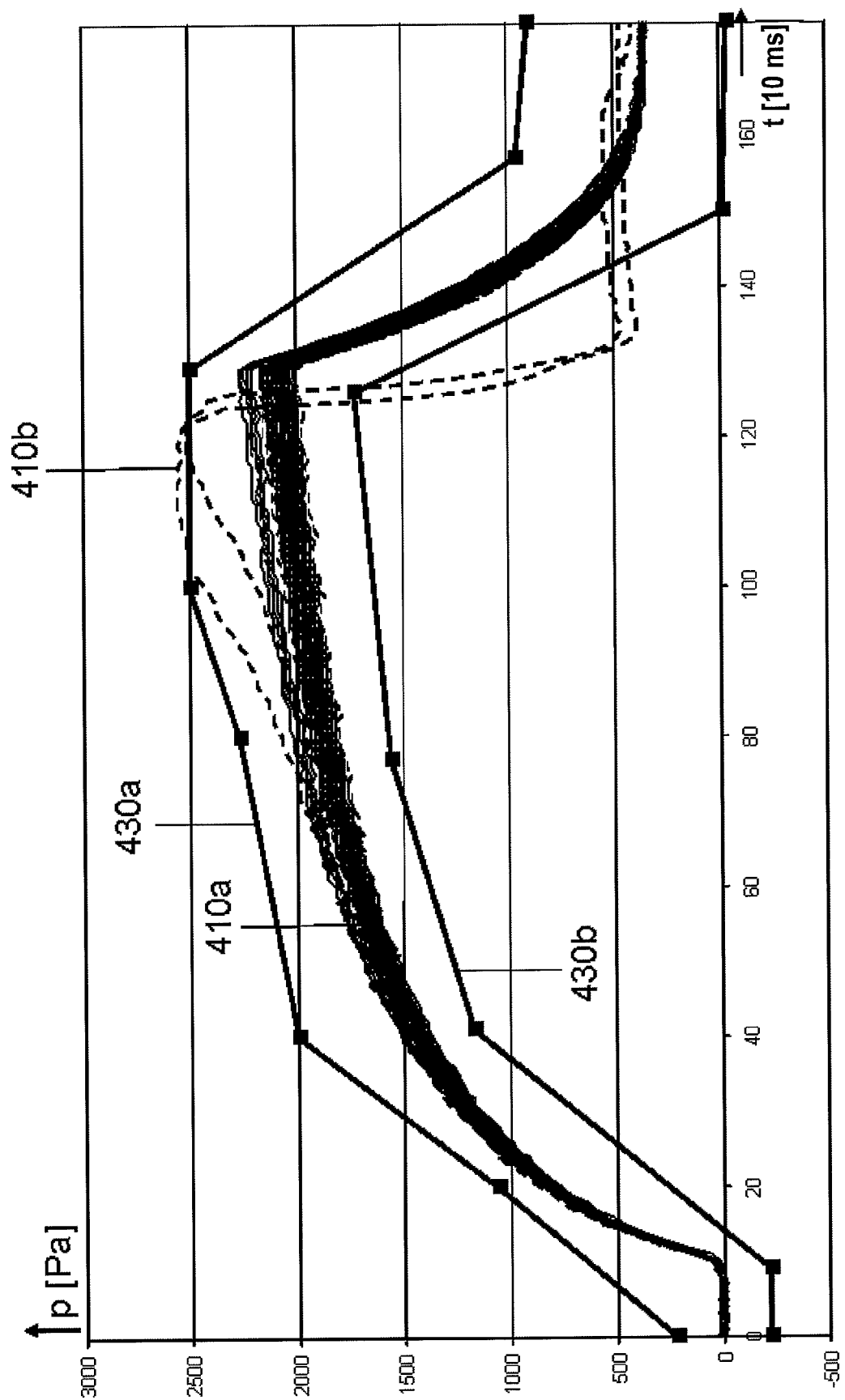

In FIG. 5, a dispensing process is shown with a family of standard pressure courses 410a. Further, FIG. 5 shows an upper curve 430a and a lower curve 430b defining an allowable pressure profile. Like in FIG. 4, two family groups can be identified, each relating to different standard processes. The difference can be caused by dimension variances due to the manufacturing process of the respective tips. However, in contrast to FIG. 4, both family groups have the same reference sign 410a. Curves 410b, which are shown as dashed lines, relate to a dispensing process including foam. Foam can be generated in an aspiration process if the external liquid is not sufficient and additional gas, e.g. air, is pulled into the pipette, together with some of the external liquid. It can be seen from FIG. 5 that foam has a higher viscosity than liquid. This leads to a higher overpressure, in particular at the end (700 ms<t<1200 ms) of a first relaxation period between t=100 ms (start of overpressure generation) and t=1200 ms (end of overpressure generation=start of a second relaxation phase). As it can be seen from FIG. 5, the overpressure in a dispensing process with foam (dashed lines) is significantly higher than the overpressure in a dispensing process without foam (continuous line, 410a). In particular with high density foam, an overpressure situation occurs as depicted in FIG. 4. For low density foam, the slope of the pressure increase would be lower than the slope of curves 410a (not depicted). According to the amount of foam, the pressure course crosses the upper curve 430a significantly (upper curve of 410b) or only touches the upper curve 430a (lower curve of 430a). According to the invention, one or more of the interpolation points (shown as squares) of the upper curve can be displaced or added to modify the degree of allowance according to the maximum allowable deviation. Since not all errors lead to a strong (positive or negative) deviation, the width of the allowable pressure profile should be small (equivalent to a low tolerance), in particular between 800 ms and 1200 ms. Further, in order to reproduce the minimum and maximum limit course (equiv. to σ=const, e.g. 6 S) with a higher precision in sensitive areas or in areas, in which not all errors lead to a high deviation, a higher density of interpolation points could be used. In general, the allowable pressure curve in sensitive areas is for example defined by a higher density of interpolation points than in other areas. The density of interpolation points, i.e. the distance between adjacent interpolation points along the t-axis, can be adapted to the sensitivity, process section or shape of the test pressure curves and/or the maximum/minimum limit course.

In the subsequent course of the pressure course, i.e. t>1200 ms, the pressure course shows a rapid decrease and crosses the lower curve, according to a relaxation process (the $2^{nd}$ relaxation process as defined above) with a pressure compensation based on gas transfer. Thus, a dispensing process with foam provides a pressure course with a first crossing of the upper curve 430a, followed by a second crossing of lower curve 430b. In comparison thereto, FIG. 3 related to insufficient liquid volume only shows a crossing of lower curve 230b. Thus, both errors can be distinguished easily. In particular, high density foam can be distinguished from low density foam by identifying, which of the upper or lower curve has been crossed. Further, the high slope of the pressure course 410b for 700 ms<t<1150 ms as well as the detection of an inflexion point, corresponding to a value of the second derivative of the pressure course during this time interval outside an tolerance interval (defined by respective interpolation points) can be used to detect the presence of foam. These mechanisms can be used in combination with or as an alternative to the monitoring of the pressure course as described above.

Figure 6:
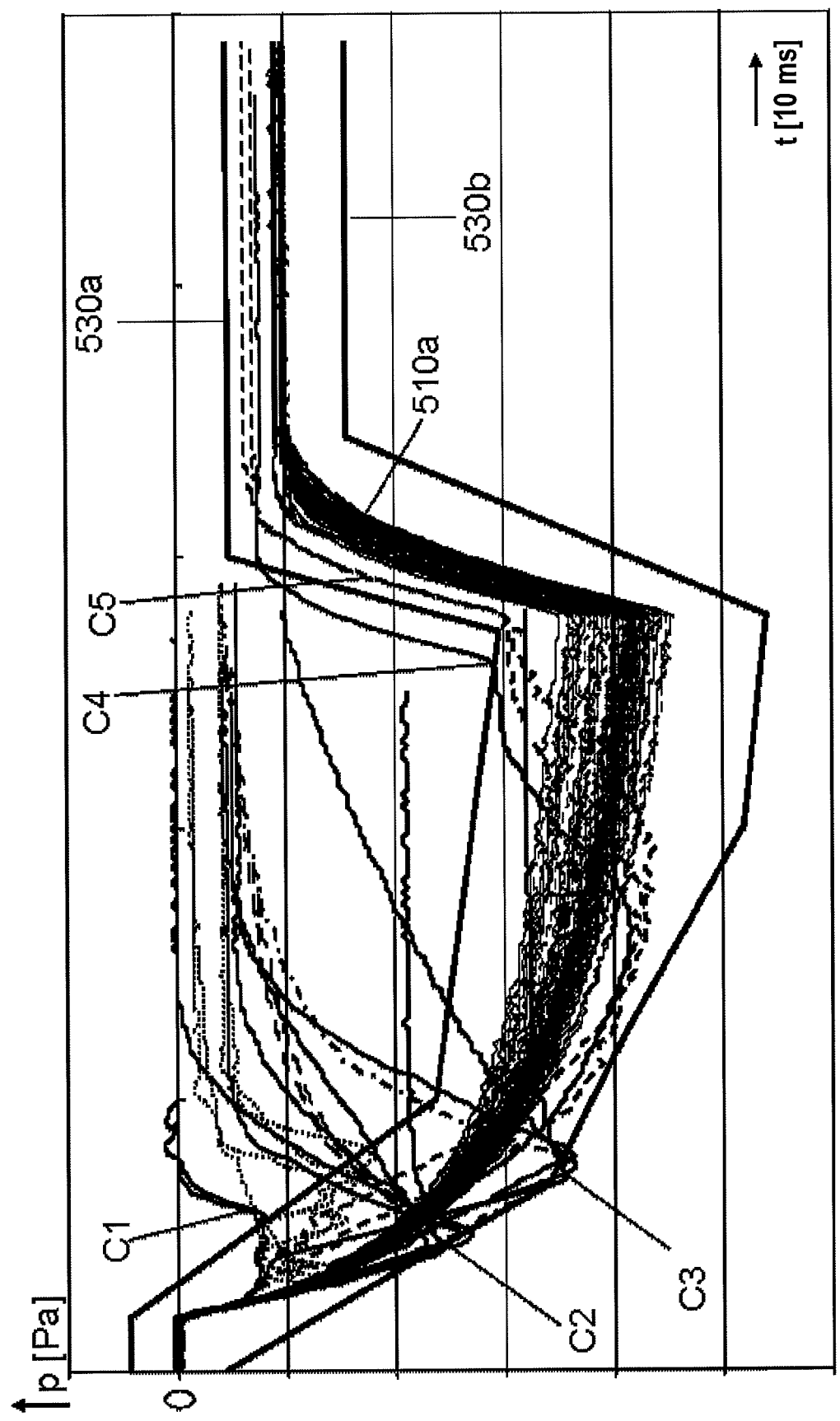

In FIG. 6, a family of standard pressure courses 510a are depicted, together with an upper curve 530a and a lower curve 530b together defining the allowable pressure profile. FIG. 6 relates to pressure courses of an aspiration process. Upon entry of gas into the pipette due to lack of external liquid, the increase of pressure is less than the standard increase. The corresponding pressure courses, e.g. C1 and the curves shown as dotted lines, cross the upper curve 530a which leads to an error signal and the immediate termination of the aspiration process. Upon entry of foam into the pipette, the increase of pressure is higher than the standard pressure increase, depending on the density of the foam. For high density foam, the pressure decrease is higher than for low density foam and for liquid. For low density foam, the pressure decrease is lower than for high density foam and for liquid. In this way, the density of foam can be identified. Further, the medium entering the pipette upon immersion, i.e. foam or liquid, can be identified. The pressure courses C2 and C3, which can be interpreted as foam aspiration curves as regards the increase of pressure, cross the lower curve 530b leading to an error signal and the immediate termination of the aspiration process. Additionally, the aspiration of clotted blood or other solid probe material also leads to an abnormally high increase of vacuum pressure which in turn leads to a pressure exceeding the upper curve. For example curve C3 shows such an increase, upon which the pressure generation is terminated. It can be seen from C3 that the pressure compensation subsequent to the termination is significantly slower due to the clotted sample liquid perturbing the flow of fluid. Further, C2 shows an increase which could be interpreted as clotting. Upon termination of pressure generation, C2 approximates an asymptote of a high vacuum pressure, which can also be used as an indication of clothing. However, if the amount of aspirated foam is acceptable and is combined with entry of sufficient liquid, the pressure increase is slightly higher in comparison to standard increases and does not lead to a termination due to violation of the lower curve 530b. Examples therefore are C4 and C5. However, due to the reduced total amount of liquid in a mixture of foam and liquid, the aspiration process ends earlier than with standard aspiration processes and, consequently, leads to an early pressure decrease. Due to the early decrease, pressure course C4 (continuous line) crosses the upper curve 530a which leads to an error signal and the termination of the aspiration process. Pressure course C5 (dotted lines) shows an abnormal pressure decrease being of a lesser extend and starting later than the detected abnormal pressure decrease of curve C4. Thus, C5 completely lies within the allowable pressure profile and is not detected as abnormal curve. The method according to the invention allows to adapt the interpolation points to this kind of error, e.g. by moving the interpolation point at the point located at the lowest position of upper curve 530a to a lower level. This would lead to a higher precision for the detection of foam, but would also lead to the false rejection of non-abnormal deviations of standard pressure courses. Thus, the aspiration of foam could be detected by monitoring the slope during the end of the first relaxation period during which standard pressure courses have a very low slope, in comparison to foam aspiration curves, which suddenly show a strong decrease of low-pressure at the point of time at which gas located above the foam enters the pipette. In order to detect such defects, an allowable pressure slope profile defined by interpolation points as described above with regard to allowable pressure profiles could be used. In FIG. 6, the squares depicting the interpolation points have been omitted for clarity reasons. However, the allowable pressure profile of FIG. 6 is for example defined by the interpolation points depicted in FIGS. 2 and 4.

FIGS. 1-6 show aspirating and dispensing processes of sample liquid or reagent or another liquid related to biochemical or chemical or physical processes with a relatively high precision as regards the liquid volume. Thus, the allowable pressure profile is relatively narrow and should be precisely defined. As mentioned above, for sensitive areas or sections and for providing a high precision in error detection, the allowable pressure profile should be exactly defined. The exactness of the definition of the allowable pressure profile can be adjusted by the density and/or number of interpolation points. Further, for sensitive areas, the interpolation points can have a smaller distance to the maximum/minimum limit course than for areas or sections with less precision. The distances can be derived from predefined minimum distances between maximum/minimum limit course and interpolation point. In comparison thereto, processes like washing, sip-and-spit, aspirating or dispensing buffer solution or similar processes might not require a high precision as regards the liquid volume. Consequently, the higher tolerance leads to a wide allowable pressure profile. Additionally, small amounts of liquid inherently involve higher variances among standard pressure processes. In order to avoid a high number of false rejections, also the handling of small amounts involves a higher tolerance leading to a wide allowable pressure profile. Further, in particular with periodic pressure curves (e.g. sip and spit), the definition of the interpolation points should reflect additional shifts due to jitter, i.e. variations regarding the starting point of the process or the first "sharp" bend of the pressure course. However, in a certain embodiment, all processes are monitored with the same precision and the same sensitivity regarding the identification of errors leading to invalid test results. Test results comprise any test results of biochemical tests.

Figure 7:
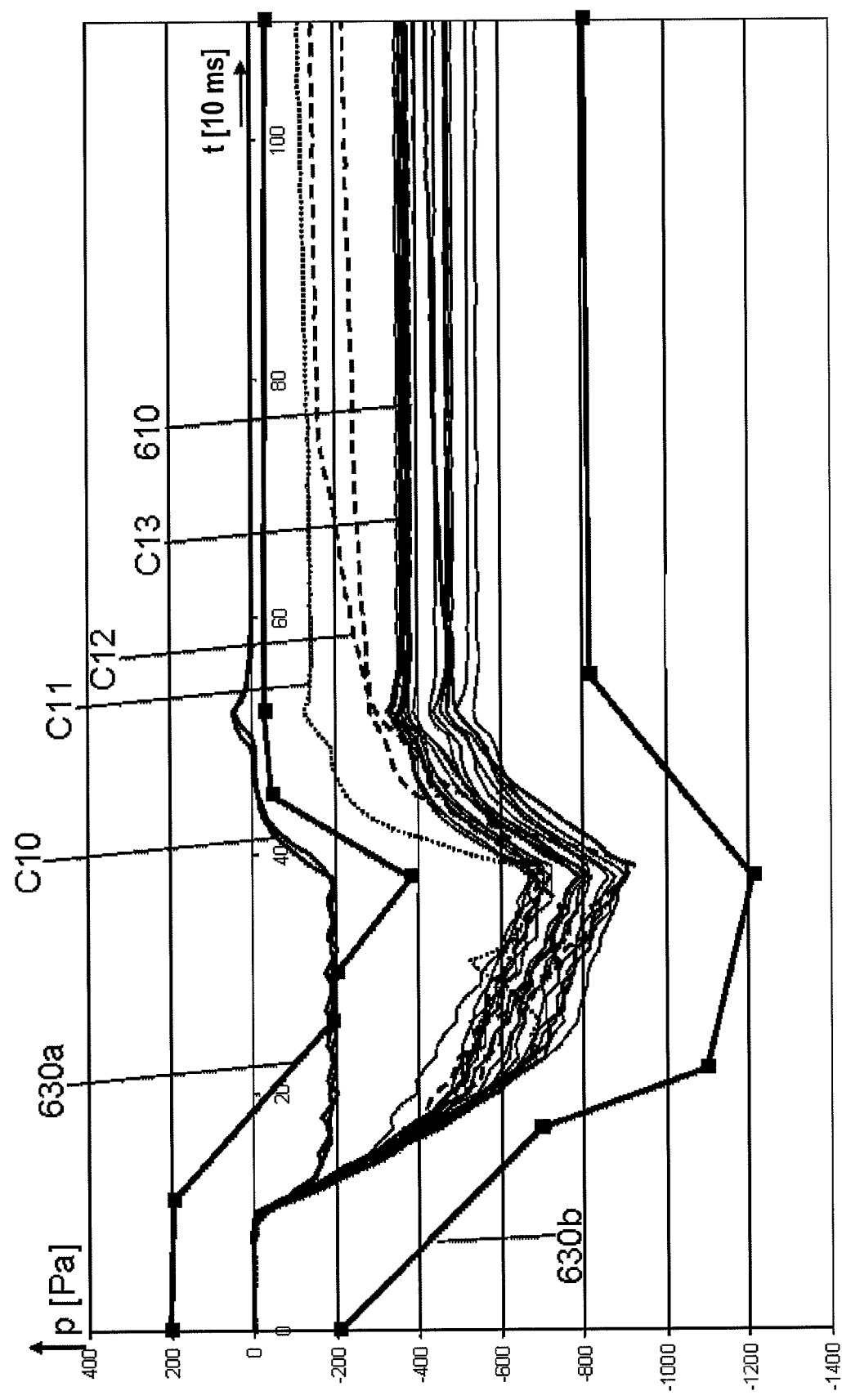

FIG. 7 depicts an aspiration process with a small volume and related to a buffer solution containing solid particles, e.g. magnetic beads. In FIG. 7, the opening of the pipette tip is close to the bottom of the solution receptacle which leads to additional fluctuations. Due to the substantial provocations (small distance between tip and bottom, solid particles in the solution), high variations occur which lead to high tolerances in the allowable pressure profile. Further, the type of error can be detected and displayed by addressing the area or section in which the pressure curve crosses the upper or lower curve. Thus, the upper curve 630a and the lower curve 630b, together defining the allowable pressure profile, provide a large tolerance interval. In the process of FIG. 7, liquid provided in a sample processing unit is aspirated, the liquid having a standard volume of 85 µl comprising liquid and solid particles, i.e. magnetic beads. Pressure course C10 is related to an empty sample processing unit. The vacuum pressure established in the pipette does not increase over a level of −200 Pa. Thus, C10 crosses the upper curve 630a at approx. t=28 ms. With regard to the standard volume, curves C11 (dotted), C12 (dashed) and C13 (continuous line) related to a deficiency 60 µl, 50 µl and 40 µl, respectively. Due to the high variances, the allowable pressure profile gives a low standard as regards the precision. Thus, the deficiency curves C11, C12 and C13 do not cross the upper or lower curve 630a, 630b. However, since the deficits of 60 µl, 50 µl and 40 µl are not crucial to the result of the underlying biochemical, chemical or physical process, the lack of any error signal is acceptable. However, C10 relates to a complete deficit of liquid volume, which is crucial to the underlying process. Therefore, it is acceptable and necessary to detect an error at approx. t=28 ms.

FIG. 7 is an example for a monitoring process with higher tolerance than FIGS. 1-6. In FIG. 7, only a few errors can detected, for example a total lack of liquid in the sample processing unit. All other derivations from the standard pressure course are tolerated since they are not significant to the process. Thus, the present invention also allows to adapt the tolerance and the precision of the monitored fluid transfer process to the needs and the importance of the monitored process step. As can be seen from the upper and lower curves 630a, b, the position of the respective interpolation points as well the shape of the resulting curves differ significantly from the interpolation points of e.g. FIGS. 2, 4, 6. Since the processed volume is significantly smaller, the process depicted in FIG. 7 is carried out faster than the process of FIGS. 2, 4, 6.

FIGS. 1-7 show dispensing processes having a positive pressure course as well as aspiration processes having a negative pressure course. In negative pressure courses the vacuum pressure is monitored and in positive pressure courses, the overpressure is monitored. Therefore, the lower curve of the allowable pressure profile related to positive pressure courses has the same functions as the upper curve of the allowable pressure profile related to negative pressure courses, i.e. an interpolated minimum performance limit. In a complementary way, the upper curve of the allowable pressure profile related to positive pressure courses has the same functions as the lower curve of the allowable pressure profile related to negative pressure courses, i.e. an interpolated maximum performance limit. Due to symmetry reasons, the upper curve of a negative pressure profile can be used as a lower curve of a positive pressure profile and vice versa, with or without additional correction scales, biases or shifts along the t-axis to adapt an allowable pressure profile of a dispensing process to an allowable pressure profile of an aspiration process. Further, the upper and the lower curve can be adapted from a high volume process (e.g. <800 μl, 850 μl or 1000 μl) to a low volume process (<300 μl) by upscaling or downscaling the respective lower or upper curve or vice versa to broaden or to narrow the tolerance width reflected by the allowable pressure profile. In this way, storage costs can be reduced and/or the precision can be improved.

FIGS. 1, 3 and 5 show a dispensing process with identical upper and lower curves 30*a, b*; 230*a, b* and 430*a, b*. The upper curve of a dispensing process is defined by 8 interpolation points and the lower curve of a dispensing process is defined by 7 interpolation points. According to the invention, also 3, 4, 5, 6, 7, 9, 10, 11-15 or 16-20 interpolation points can be used for the upper curve of a dispensing process. Further, according to the invention, also 3, 4, 5, 6, 8, 9, 10, 11-15 or 16-20 interpolation points can be used for the lower curve of a dispensing process. For example, less than 5, 10, 15, 25, 30, 50, 100 or 200 interpolation points are used per second.

Further, FIGS. 2, 4, 6 show an aspiration process with identical upper and lower curves 130*a, b*; 330*a, b* and 530*a, b*. The upper curve of an aspiration process is defined by 6 interpolation points and the lower curve of a dispensing process is defined by 8 interpolation points. According to the invention, also 3, 4, 5, 7, 8, 9, 10, 11-15 or 16-20 interpolation points can be used for the upper curve of an aspiration process. Further, according to the invention, also 3, 4, 5, 6, 7, 9, 10, 11-15 or 16-20 interpolation points can be used for the lower curve of an aspiration process. For example, less than 5, 10, 15, 25, 30, 50, 100 or 200 interpolation points are used per second.

Like FIGS. 2, 4 and 6, FIG. 7 shows an aspiration process. However, in comparison to the process of FIGS. 2, 4 and 6, the process of FIG. 7 is monitored with less precision and higher tolerance intervals and is carried out with a reduced liquid volume. The upper curve of the aspiration process of FIG. 7 is defined by 8 interpolation points and the lower curve of the dispensing process of FIG. 7 is defined by 6 interpolation points. However, other number can be used as defined with regard to FIGS. 2, 4 and 6.

According to the invention, less than 25, 30, 40, 50, or 100 interpolation points are used per lower or upper curve. Further, the minimum distance between two consecutive interpolation points of the same curve can be higher than 200 ms, 100 ms, 50 ms, 20 ms or 10 ms. In a certain embodiment, the distance between a pair or consecutive interpolation points significantly differs from the distance between another pair of two consecutive interpolation points of the same curve by at least 5%, 10%, 20% or 40%.

Figure 8:
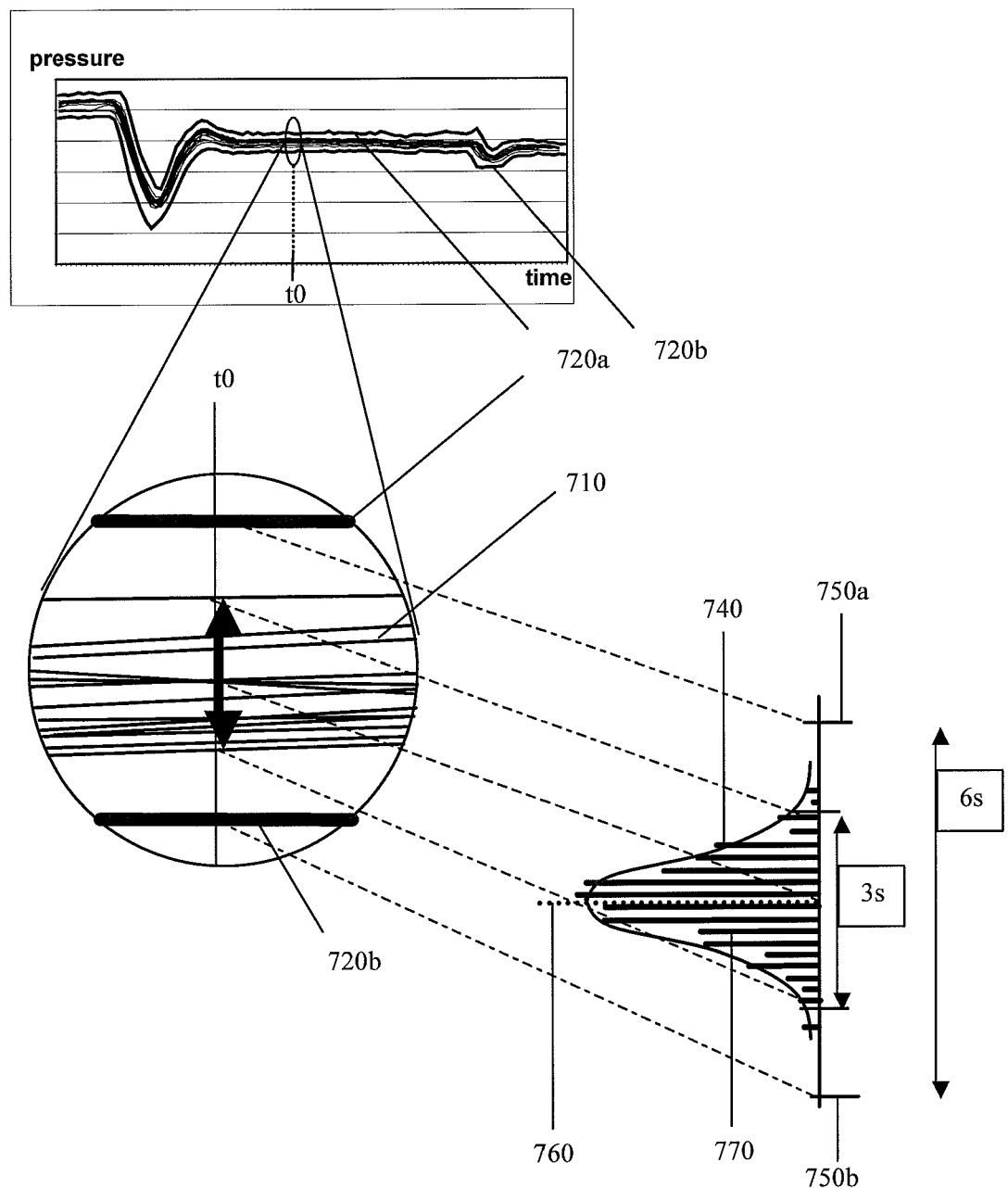
FIG. 8 shows a family of pressure courses, together with the distribution and the minimum and maximum limit course derived therefrom.

FIG. 8 shows a family of pressure courses 710, together with the distribution 740 and the minimum and maximum limit course 750 *a, b* derived therefrom. As already discussed with regard to FIGS. 1-7, a number of standard pressure courses are measured. The measurements are carried out at standard conditions and with the same pipette/pipette tip or with pipette tips of the same batch. In FIG. 7, the pressure courses are measured at three different temperatures, i.e. at 18° C., 24° C. and 34° C. to address the variance resulting from the temperature variances. Of course, the pressure courses can be measured at a single temperature. All pressure courses begin at the same process phase and, consequently, are synchronised.

As can be seen from the diagram in the upper left corner of FIG. 8 as well as from the detailed view related to a certain point of time depicted in the circle below the diagram, the pressure courses vary and form a statistical distribution. For reasons of clarity, only a few courses are depicted. However, if more than 20 courses (for example more than 100 or 350) are measured, a significant frequency distribution is provided having a Gaussian shape. The Gaussian shape is a result of the plurality of causes leading to the measured pressure. Of course, other distributions, e.g. a Poisson distribution, a symmetrical distribution or another unsymmetrical distribution can be the result of the process. One of the above mentioned distribution or an approximated distribution involving low calculation costs, e.g. raised cosine, can be used as a basis for the calculation of the minimum and the maximum limit. For one or a plurality of point of times (t0), the actual frequency distribution 770 is calculated from the family of courses 710. The frequency distribution provides the number of pressure courses falling in a certain pressure value interval. In FIG. 8, all occurring pressure values for t=t0 are assigned to respective intervals, the intervals being represented in FIG. 8 by 20 lines. The length of the line corresponds to the respective number of hits, i.e. number of measured courses falling in the respective pressure value interval. Of course, other resolutions can be used.

In a first embodiment, the corresponding Gaussian distribution 740 is defined by mean value m (c.f. reference sign 760), and variance s or σ. Thus, the mean value m denoted with reference sign 760 is calculated by adding all pressure values of the plurality of pressure courses 710 and dividing the sum by the number of courses. The variance is defined by the square root of the sum of all squared pressure differences between mean value and actual pressure course value. Further, a scale factor is used, together with the Gaussian function having the parameters m and s, to approximate the Gaussian function to the actual frequency distribution of the pressure courses.

In a second embodiment, the numbers of pressure values falling in respective intervals as depicted with reference sign 770 can be used as a basis for approximating a probability mass function, e.g. a Gaussian distribution or other distributions. The distribution can be adapted to the measured frequency distribution 770 related to discrete pressure intervals by any approximation or interpolation method including iterative methods, e.g. least mean error, or by any predefined approximation methods including polynomial interpolation or by predefined probability distribution functions being defined by parameters, which can be optimized in order to reduce the error between function and measured frequency distribution to a minimum. In contrast to the first embodiment, the second embodiment involves the calculation of a discrete measured frequency distribution as an intermediate result and the adaptation of an approximation function to the shape of the measured distribution.

According to the invention, both pressure values related to a standard deviation related to a variance of ±1.5 σ, ±3 σ or ±6σ or any other predefined probability limit 750*a, b*, are derived from the approximated or calculated probability distribution function. Further, the pressure values related to values prob and 1-prob, prob being a certain probability, are derived from the approximated or calculated probability distribution function.

The derived pressure values define the minimum limit 720*b* and the maximum limit 720*a*. The maximum limit and the minimum limit can be used to define respective interpolation points; however, additional or alternative methods can be used to define the interpolation points. In one embodiment, at least one of the minimum limit and the maximum limit is used to define the interpolation points at a point of time corresponding to the maximum variance. In another embodiment, the pressure value as well as the time value of the minimum limit and/or the maximum limit is identical with corresponding values of a respective interpolation point or a pair or respective interpolation points.

According to the invention, the maximum limit as well as the minimum limit is calculated for a plurality of points of time continuously forming a maximum limit course and a minimum limit course. In another embodiment, resolution of limit courses, i.e. the periodicity of the points of time or sample points is reduced forming an approximated sampled maximum and minimum limit course. Further, the maximum limit as well as the minimum limit can be calculated for only a few predefined points of time. In the detailed diagram FIG. 8 shown in the lower half, the minimum limit 720b as well as the maximum limit 720a is calculated and defined for t=t0±δ. In the overview diagram shown in the upper left corner of FIG. 8, the minimum and maximum limits are depicted as continuous courses 720 *a, b*, which are continuously provided for all time values. The minimum and maximum limits can be calculated with a periodicity of at least 1/0.1 ms, 1/1 ms or 1/10 ms to provide limit data with an accuracy adapted to the shape and the (maximum) slew rate of the monitored pressure courses.

Figure 9:
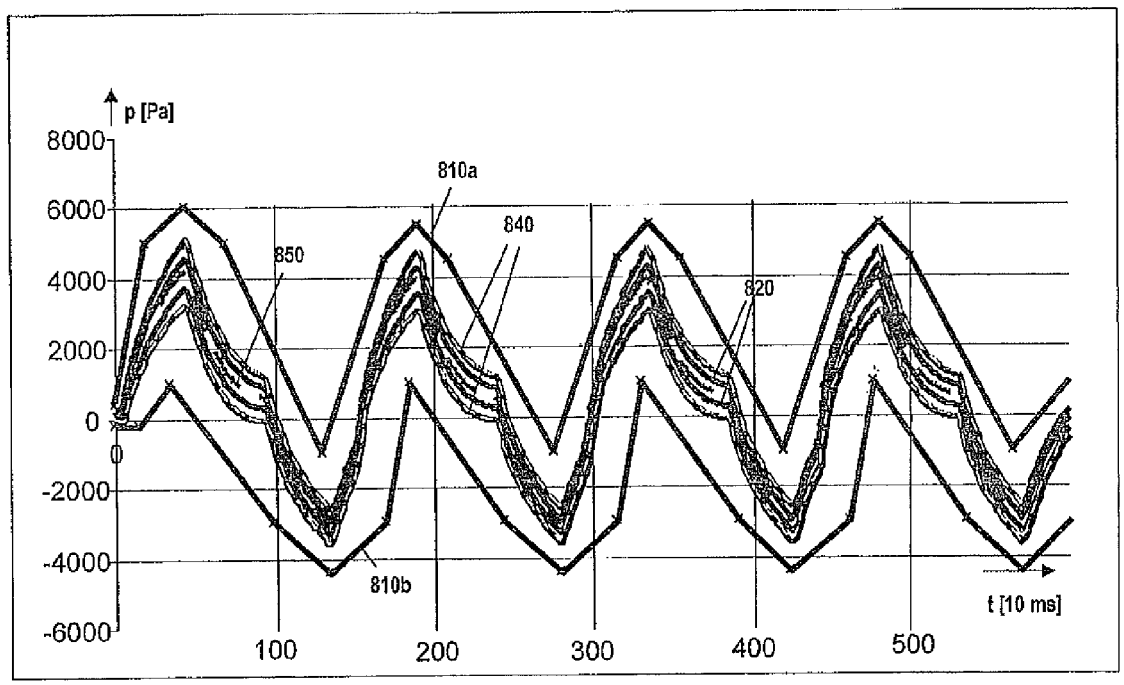

FIG. 9 shows a periodic sip-and-spit process comprising alternating aspiration and dispense processes. The interpolation points are depicted as crosses. The allowable pressure profile is defined by an upper curve 810a and a lower curve 810b. The mean pressure of a plurality of test runs corresponds to the reference, i.e. target pressure curve and is depicted as dashed line 850. As mentioned above, a family of test curves has been statistically evaluated to obtain the Gaussian distribution of the pressure curves as a function of (process) time t. The function of time, i.e. the curve corresponding to the obtained Gaussian distribution with a fixed variance, e.g. 3 sigma and 6 sigma, shown with reference signs 820 (3 sigma) and (as another example) 840 (=6 sigma) precisely reproduce the statistical behaviour of the pipette system. Thus, one of the curves 820 or 840 is used as a basis for the interpolation points forming the upper curve 810a and the lower curve 810b since the pressure curves related to a predefined variance of the empirically obtained Gaussian distribution provide a precise means for distinguishing between normal behaviour including some fluctuations and abnormal behaviour resulting from a malfunction of the pipette system. Since the allowable pressure profile is periodic, the interpolation points of a first peak can be copied and shifted along the time axis t to form a section of the allowable pressure profile for a subsequent section. Further, as it can be seen from FIG. 9, the statistical behaviour is exactly repeated in the consecutively repeated process phases.

In general, the derivation or calculation of maximum/minimum limits from a family of pressure courses shown in FIG. 8 and described in the respective description passages can be used for any of the processes shown in FIGS. 1-7 and 9. In particular, the maximum/minimum limits can be used for defining at least one or all interpolation points depicted in FIGS. 1-7 and 9.

The figures show diagrams showing the pressure p(t) on the y-axis in the course of time, depicted on the x-axis as t. Both axes are drawn in linear scale, however, in certain embodiments, the y-axis being assigned to the pressure can be depicted in a logarithmical scale.

In general, the interpolation points is selected to generate a rejection rate of approx. 0.2% or less than 0.2% for non-erroneous samples/pipettes or for a group of samples/pipettes with average or normal variances, error probabilities and other stochastical properties. The predefined variance or another statistical parameter and/or the predefined additional margin or additional distance can be chosen in order to provide such a rejection rate.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A computer implemented method for monitoring a fluid transfer process, comprising:
    providing an allowable pressure profile on a storage device, wherein the providing an allowable pressure profile comprises:
        acquiring a family of pressure courses as a function of time of a plurality of fluid transfer processes, and
        providing a frequency distribution of the acquired family as a function of time and determining a minimum limit course and maximum limit course corresponding to a predefined value of the at least one statistical parameter of the family, wherein at least one of the interpolation points is a point of one of the limit courses and all interpolation points are external to the area confined between the minimum limit and the maximum limit, the at least one statistical parameter comprising the variance of the family of pressure courses;
    detecting, by way of one or more pressure sensors, a pressure occurring in the course of the fluid transfer process;
    comparing the detected pressure with the allowable pressure profile;
    signaling an error, if the detected pressure is not within the allowable pressure profile;
    wherein the allowable pressure profile is defined by interpolation points, the interpolation points being based on a probability function representing a family of pressure courses of a plurality of fluid transfer processes.

2. The method according to claim 1, wherein the fluid transfer process is a pipette process including aspirating and dispensing.

3. The method according to claim 1, wherein the probability function is a function of time and is defined by at least one statistical parameter of the family of pressure courses, the pressure courses being test pressure courses of a plurality of pipette processes carried out in the same or in comparable or similar pipette systems.

4. The method according claim 1, wherein determining the minimum limit and the maximum limit course comprises:
    extrapolating the family of pressure courses onto a course of a time-dependent Gaussian distribution of pressure values, the minimum and maximum limit courses corresponding to the course of the Gaussian distribution at the predefined variance.

5. The method according to claim 1, wherein the allowable pressure profile is divided into at least two distinct process sections of the fluid transfer process; and each section of the allowable pressure profile is defined by a subset of interpolation points, each subset being specific to a corresponding one of the distinct process sections.

6. The method according to claim 5, wherein each section of the allowable pressure profile is defined by at least one straight line comprising two interpolation points of the respective subset.

7. The method according to claim 1, wherein the allowable pressure profile is formed of an upper curve and a lower curve, each being interpolations of interpolation points, or the allowable pressure profile is formed of a base curve being defined by interpolation points and at least one set of corresponding relative values defining the tolerance width of the allowable pressure profile as a function of time, or the allowable pressure profile is formed of interpolation points and a set of corresponding slopes.

8. The method according to claim 1, wherein the allowable pressure profile is defined by linear interpolation or by polynomial interpolation of the interpolation points or by linear interpolation or by polynomial interpolation of a set of tolerance widths interpolation values in combination with linear interpolation or polynomial interpolation of the interpolation points.

9. The method according to claim 1, wherein the interpolation points are coordinates formed of a pressure value/time value pair or wherein the interpolation points are factors of a series expansion or further comprise factors of a polynomial interpolation.

10. The method according to claim 1, wherein signaling an error comprises:
    determining the process section, in which the detected pressure exceeded or undershot the allowable pressure profile, and
    providing information about a process phase corresponding to the determined process section.

11. The method according to claim 1, wherein the fluid transfer process comprises:
    varying a gas volume thereby moving a liquid volume, the liquid volume being in fluidic connection with the gas volume.

12. The method according to claim 1, further comprising:
    providing interpolation points corresponding to a family of pressure courses measured during a test transfer process using a batch of fluid transfer devices, wherein the monitored fluid transfer process is carried out with said batch of fluid transfer devices.

13. The method according to claim 1, further comprising:
    maintaining a data base storing a plurality of sets of interpolation points, each together with a corresponding batch number identifying the batch of fluid transfer devices and/or together with corresponding batch classification index classifying fluid transfer properties of the respective batch, wherein providing an allowable pressure profile comprises retrieving interpolation points from the data base during or before the monitored fluid transfer process.

14. The method according to claim 1, wherein at least a section of the allowable pressure profile is defined by the subset of interpolation points and by at least one property of the fluid transfer process, the at least on property comprising: volume, viscosity, temperature, surface tension or kind of the fluid transferred in the fluid transfer process, or area, length, flow resistance or usage status of a fluidic connection through which the fluid is forced in the fluid transfer process.

15. The method according to claim 1, further comprising:
    initiating a pressure measurement device by resetting the pressure measurement device on a initial value, wherein the pressure measurement device is initiated directly before the step of detecting.

16. The method according to claim 1, wherein the step of detecting comprises:
    providing an analog/digital converter with an analog pressure signal, the analog/digital converter having a minimum resolution $\delta$, wherein the first process section at the start of the fluid transfer process of the allowable pressure profile has a width greater than $2\times\delta$ and less than $20\times\delta$.

17. The method according to claim 1, further comprising the step of:
    terminating the fluid transfer process as well as suspending further fluid transfer processes, if the error signaled.

18. A non-transitory computer readable medium containing computer instructions stored therein for causing a computer to perform the steps in the method of claim 1, the computer readable medium storing interpolation points or information for directly or indirectly retrieving interpolation points from a data base or from a correspondence table, the interpolation points defining at least one of the sections of the allowable pressure profile.

* * * * *